(12) United States Patent
Chisena et al.

(10) Patent No.: US 10,792,181 B2
(45) Date of Patent: Oct. 6, 2020

(54) ORTHOPAEDIC DEVICE AND METHOD OF USE FOR TREATING BONE FRACTURES

(71) Applicants: Ernest C. Chisena, Fort Salonga, NY (US); Jahangir S. Rastegar, Stony Brook, NY (US)

(72) Inventors: Ernest C. Chisena, Fort Salonga, NY (US); Jahangir S. Rastegar, Stony Brook, NY (US)

( * ) Notice: Subject to any disclaimer, the term of this patent is extended or adjusted under 35 U.S.C. 154(b) by 668 days.

(21) Appl. No.: 15/400,397

(22) Filed: Jan. 6, 2017

(65) Prior Publication Data
US 2017/0181882 A1    Jun. 29, 2017

Related U.S. Application Data

(63) Continuation-in-part of application No. 13/894,688, filed on May 15, 2013, now abandoned.

(60) Provisional application No. 61/647,169, filed on May 15, 2012.

(51) Int. Cl.
| | |
|---|---|
| *A61F 5/058* | (2006.01) |
| *A61F 5/01* | (2006.01) |
| *A61B 17/132* | (2006.01) |
| *A61F 5/32* | (2006.01) |
| *A61F 5/30* | (2006.01) |
| *A61N 2/00* | (2006.01) |
| *A61B 17/64* | (2006.01) |
| *A61B 17/62* | (2006.01) |
| *A61N 1/20* | (2006.01) |

(52) U.S. Cl.
CPC ...... *A61F 5/05833* (2013.01); *A61B 17/1325* (2013.01); *A61F 5/0118* (2013.01); *A61F 5/05841* (2013.01); *A61F 5/30* (2013.01); *A61F 5/32* (2013.01); *A61B 17/62* (2013.01); *A61B 17/64* (2013.01); *A61N 1/205* (2013.01); *A61N 2/004* (2013.01)

(58) Field of Classification Search
CPC ..... A61B 17/1325; A61B 17/60; A61B 17/62; A61B 17/64; A61F 5/05841; A61F 5/30; A61F 5/05833; A61F 5/0118; A61F 5/05816; A61F 5/012; A61N 1/205; A61N 2/004; A61N 2/008
USPC ................... 602/13, 5, 2; 606/201
See application file for complete search history.

(56) References Cited

U.S. PATENT DOCUMENTS

| | | | |
|---|---|---|---|
| 5,003,969 A | 4/1991 | Azer et al. | |
| 5,171,310 A | 12/1992 | Chisena | |
| 5,746,213 A * | 5/1998 | Marks | A61B 5/02233 600/499 |

(Continued)

*Primary Examiner* — Ophelia A Hawthorne
(74) *Attorney, Agent, or Firm* — Scully, Scott, Murphy & Presser, P.C.

(57) ABSTRACT

Orthopaedic device and a method of use thereof are provided for treating a bone fracture. The orthopaedic device includes a sheet cover configured to extend over a portion of a patient's skin corresponding to a bone fracture under the skin, the sheet cover configured to form an enclosed volume between the portion of the patient's skin and the sheet cover, wherein the sheet cover comprises a vacuum port, the vacuum port configured to apply a vacuum to withdraw a gaseous volume from the enclosed volume and a member, the member configured to be in the enclosed volume, the member configured to deform in at least a direction towards the skin and apply a force to the fracture.

11 Claims, 22 Drawing Sheets

(56) References Cited

U.S. PATENT DOCUMENTS

| | | | |
|---|---|---|---|
| 5,904,219 A * | 5/1999 | Anahid | A47C 31/126 |
| | | | 180/273 |
| 6,171,307 B1 | 1/2001 | Orlich | |
| 2002/0145091 A1 | 10/2002 | Talish et al. | |
| 2005/0043659 A1 * | 2/2005 | Challis | A61F 5/012 |
| | | | 602/5 |
| 2006/0276789 A1 | 12/2006 | Brinker | |
| 2011/0125071 A1 | 5/2011 | Chisena et al. | |
| 2013/0310628 A1 | 11/2013 | Chisena et al. | |

* cited by examiner

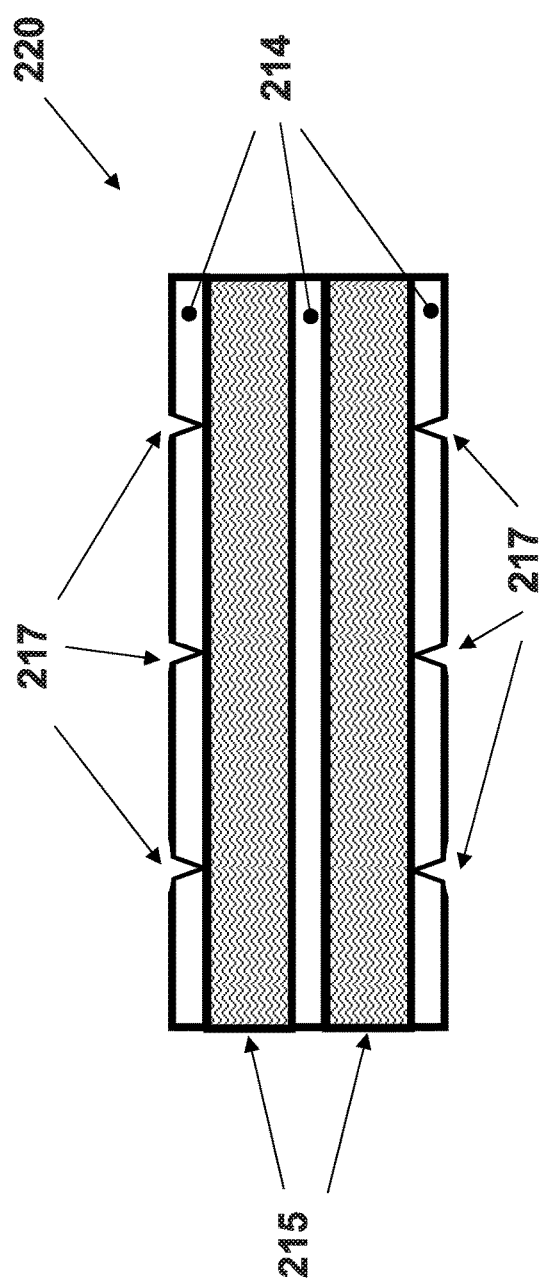
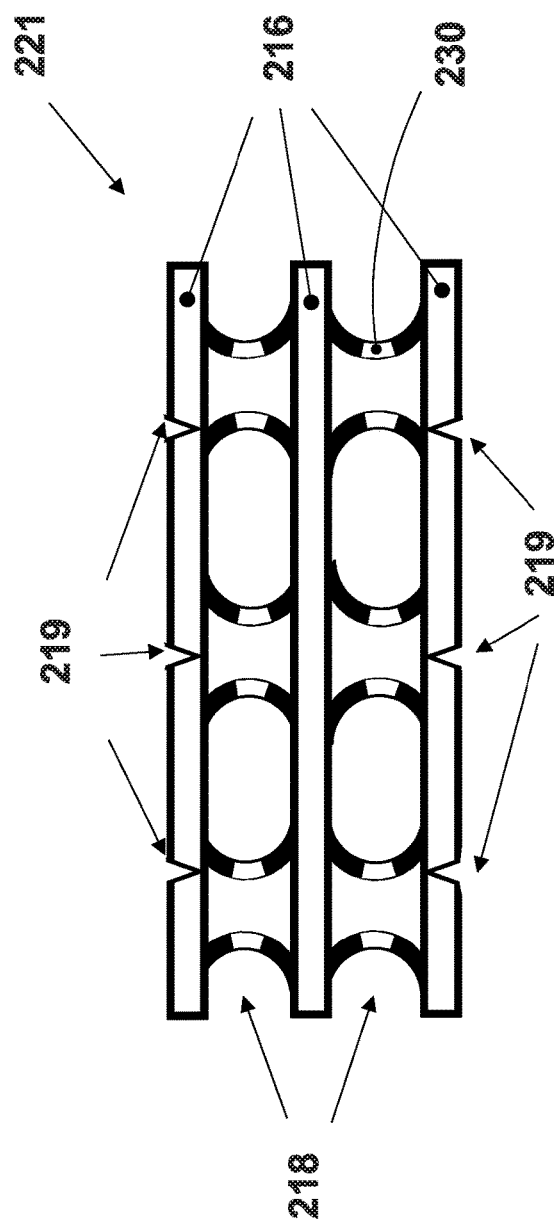

ORTHOPAEDIC DEVICE AND METHOD OF USE FOR TREATING BONE FRACTURES

CROSS REFERENCE T(I) RELATED APPLICATIONS

The present application is a continuation-in-part of a co-pending application having U.S. Ser. No. 13/894,688, filed on May 15, 2013, which claims the benefit of U.S. Provisional Patent Application No. 61/647,169, filed May 15, 2012, its entire content and disclosure of which is incorporated herein by reference.

FIELD OF THE INVENTION

The present disclosure is related generally to orthopaedic devices and methods of use thereof, for treating bone fractures.

BACKGROUND OF THE INVENTION

Currently known devices for applying pressure to soft tissue surrounding a bone fracture include a relatively soft material such as a sponge that is held against the soft tissue by a brace.

To use such devices, the sponge is positioned on the interior surface of the brace while the brace is in an untightened configuration so that when the cross-sectional dimension of the brace is reduced, the resulting position of the sponge overlies the apex of the bone fracture. In response to the reduction in diameter of the brace, a distribution of radially directed force is applied over the sponge and the sponge thereby applies a distributed pressure to the soft tissue adjacent to the bone fracture.

Such devices typically suffer from the drawback of requiring several iterations of engagement and disengagement of the brace to suitably adjust the magnitude of and the position at which pressure is applied to the soft tissue. Further, it is difficult to maintain the pressure applied to the soft tissue using such devices. Still further, the operation of such devices are complex and not user-friendly. Still further, they are limited to applying force to the soft tissues by mechanical means.

SUMMARY OF THE INVENTION

One embodiment of the disclosure is directed to an orthopaedic device and a method of use thereof are provided for treating a bone fracture. The orthopaedic device includes a sheet cover configured to extend over a portion of a patient's skin corresponding to a bone fracture under the skin, the sheet cover configured to form an enclosed volume between the portion of the patient's skin and the sheet cover, wherein the sheet cover comprises a vacuum port, the vacuum port configured to apply a vacuum to withdraw a gaseous volume from the enclosed volume and a member, the member configured to be in the enclosed volume, the member configured to deform in at least a direction towards the skin and apply a force to the fracture.

BRIEF DESCRIPTION OF THE FIGURES

FIG. 27 is a cross-sectional view of a member of the pressure applicator.

FIG. 28 is a cross-sectional view of a member of the pressure applicator.

DETAILED DESCRIPTION OF THE INVENTION

The present disclosure is related to orthopaedic devices having at least one pressure applying element configured to apply pressure to soft tissue adjacent to a bone fracture and a. holder configured, in an engaged state, to engage the soft tissue adjacent to the bone fracture and, while in the engaged state, to permit adjustable positioning of the at least one pressure applying element to the holder. The present disclosure is further related to methods of use of the orthopaedic devices described herein to treat and align bone fractures and, in particular, for accelerating the healing of bone fractures and/or mitigating the pain associated with bone fractures, through mechanisms described in U.S. Pat. No. 5,171,310.

It is understood that soft tissue may include fat, muscle, facial issue, small and large blood vessels, nerves lymphatic tissue and bone periosteum.

It is generally known that fracture healing is affected by three phenomena, mechanical pressure, electric and magnetic fields. Mechanically applied pressure alters the blood flow in the soft tissues. This changes the tissue pH and thus the concentration of free calcium ion is increased. Thus, increasing the pressure in the soft tissues results in an increase in the concentration of the free calcium ion. An electric field will result in an increase in the free calcium ion concentration by the application of an electrically induced force on the soft tissues. Additionally, an electrical field will impart a velocity to the free calcium ions. A magnetic field will also result in an increase in the free calcium ion concentration by the application of a magnetically induced force to the soft tissues while the magnetic field will impart a velocity to moving calcium ions. The present application describes devices and methods to apply one or more of the above phenomena to align an angulated fracture and to manipulate (increase) the concentration of the free calcium ions around the fracture site to accelerate its healing and mitigate pain.

Exemplary embodiments of the orthopaedic devices and methods of use thereof will be described with reference to the accompanying drawings.

First Embodiment

In a first embodiment, orthopaedic device 1, described below with reference to FIGS. 1-3, 5, 7A, 7B and 15-18, includes one or more pressure applying elements 16 and a holder 2.

The one or more pressure applying elements 16, to be described in detail below, is configured to be adjustably positioned on to the holder 2 and configured to adjustably apply pressure to the soft tissue adjacent to the bone fracture.

The holder 2 is configured to be positioned onto a target body part and to engage soft tissue adjacent to a bone fracture. It is understood that although the holder 2 is illustrated in the figures as a brace, the holder 2 may alternatively be a splint, a cast, a bandage, or a structural member that surrounds a body part, in whole or in part.

Figure 1:
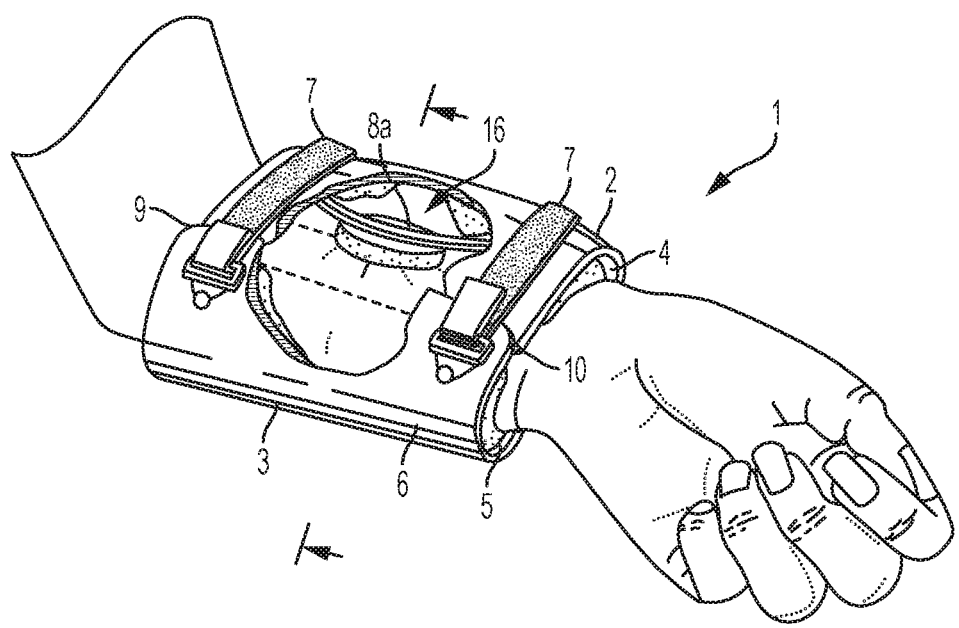
FIG. 1 shows an embodiment of the orthopaedic device that includes one access port.
Figure 2:
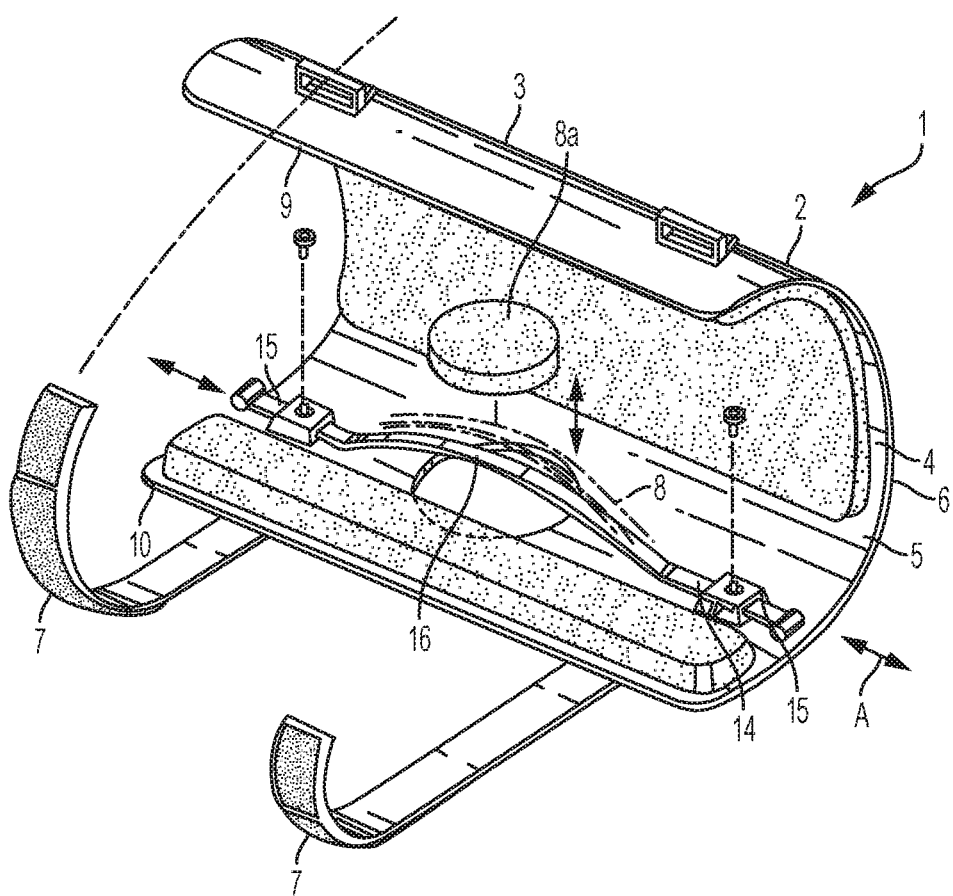
FIG. 2 shows an exploded view of the orthopaedic device of FIG. 1 with a foam pad.

As illustrated in FIGS. 1 and 2, the holder 2 has, for example, a formed open shell configuration along a longitudinal direction 3 that defines a first edge 9 and a second edge 10. The open shell configuration of the holder 2 further defines longitudinal openings 4 at a first and second end of the holder 2, as well as an inner surface 5 and an outer surface 6. The holder 2 is configured to be of a length and width for encircling a target body part in whole or in part therein. Further, the holder 2 is substantially rigid in the longitudinal direction 3 and is thus suited to laterally support the target body part and align an angulated fracture.

Figure 15:
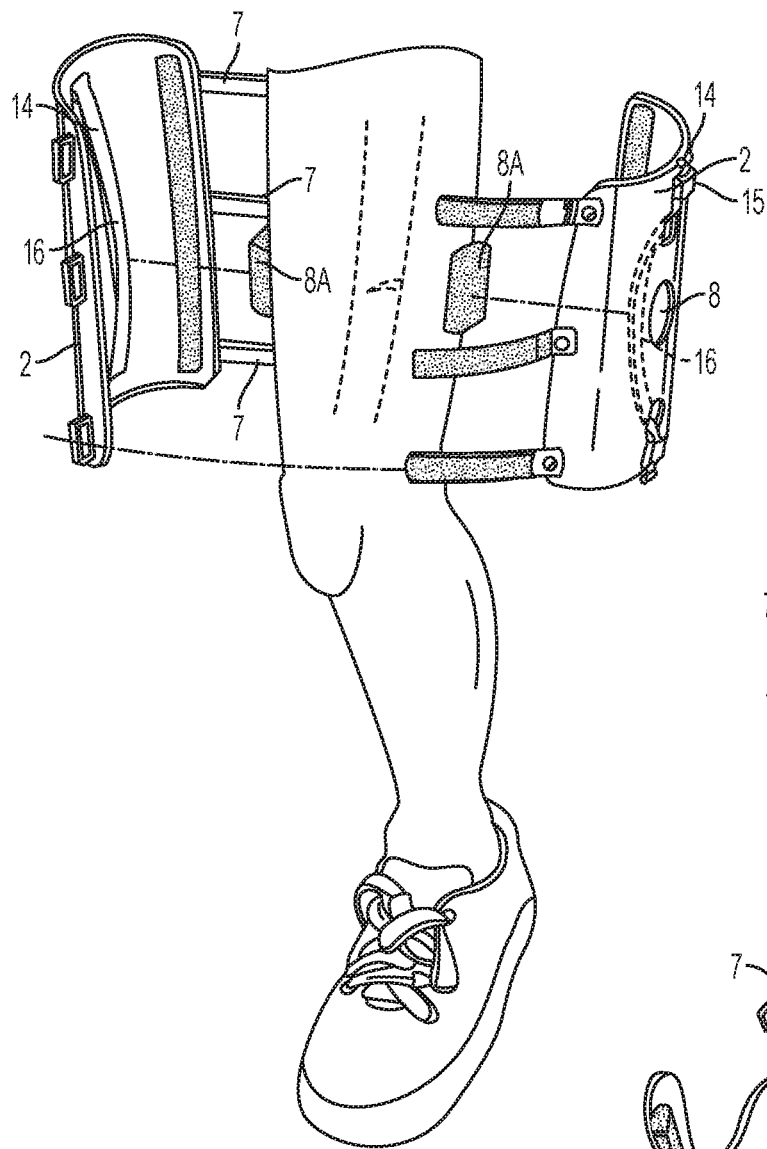
FIGS. 15 through 18 show the orthopaedic device being applied to a leg bone fracture with different holder configurations.
Figure 16:
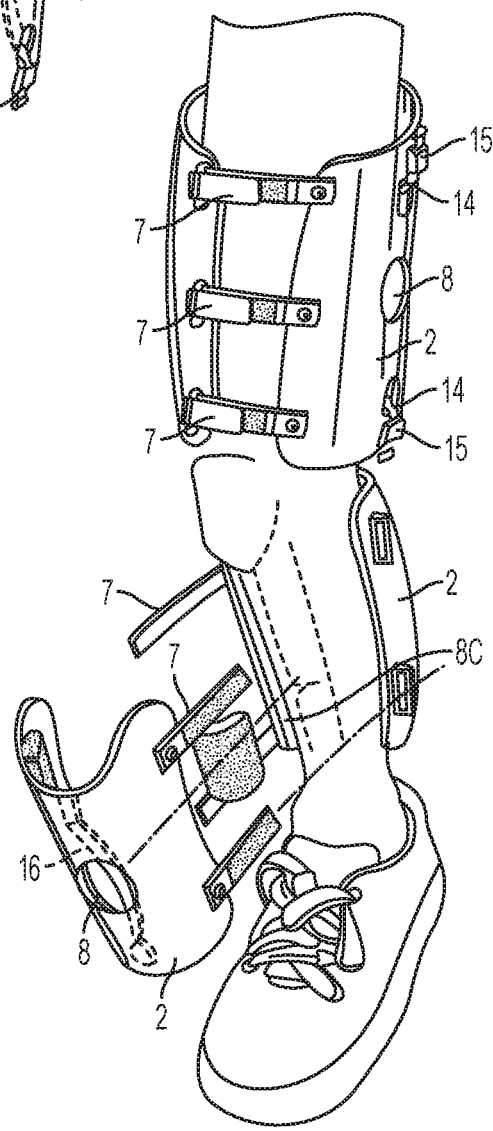

As illustrated in FIGS. 15 and 16, the holder 2 may be constructed with more than one formed open shell sections and/or annular sections so as to divide the holder 2 into two or more parts, which may be completely or partially separated. Where the holder 2 is composed of two or more parts, the parts can be configured such that, when engaged, the parts surround a target body part with one more bone fracture.

The holder 2 further includes a cross-sectional adjustment mechanism 7 including, for example, an adjustable strap wound through a loop, a loop and hook material such as VELCRO® (see FIGS. 1 and 2), a locking or clipping mechanism, a snap-fit, a button, a lacing, a zipper, or a ratcheted-type of mechanism, or any other type of mechanism known in the art.

The cross-section adjustment mechanism 7 can be operated to apply a hoop stress to holder 2 to reduce the cross-sectional dimension of the holder 2 to thereby fit and secure the holder 2 to the target body part. In this engaged state, the holder 2 is further configured to facilitate adjustably positioning the one or more pressure applying elements 16 to the holder 2 and to sustain the radially-directed pressure applied by the one or more pressure applying elements 16 to the soft tissue adjacent to the bone fracture.

In a first example of the orthopaedic device 1 of the present embodiment, the holder 2 includes an access port 8, which extends through (i.e., through the outer surface 6 and through the inner surface 5) of the holder 2. The access port 8 is configured to have a dimension suitable for permitting a pressure applying element 16 to operate therethrough or to be adjusted therethrough to position and apply a localized pressure onto soft tissue surrounding a bone fracture, either directly or through pressure applied to an intermediary contact material (described in further detail below) which then distributes the applied pressure onto the soft tissue.

The access port 8 facilitates adjustment of the pressure applying element 16 through the access port 8 so the holder 2 need not be removed once it is positioned and secured in an engaged state on a target soft tissue. As illustrated in FIGS. 1 and 2, the access port 8 in the orthopaedic device 1 allows pressure to be applied and suitably adjusted in a localized manner from outside the holder 2 through the access port 8 after the holder 2 has been fitted onto the target soft tissue.

The access port 8 disposed on the holder 2 can be of any suitable shape, which will permit a pressure applying element 16 to operate therethrough. FIG. 2 shows the access port 8 as being circular in shape, but this is meant to be merely exemplary. The access port 8 can be any suitable shape including, for example, oval, slot-shaped, square, rectangular or triangular.

The access port 8 renders the process of applying and adjusting a localized pressure onto soft tissue adjacent a bone fracture conveniently accessible to a user and/or healthcare professional. The pressure applying element 16 can be readily adjusted to maintain the pressure close to a set level. The pressure applying element 16 can also permit the user and/or healthcare professional to relieve the applied pressure in the event that the applied pressure exceeds a comfort level or other desired level.

Figure 5:
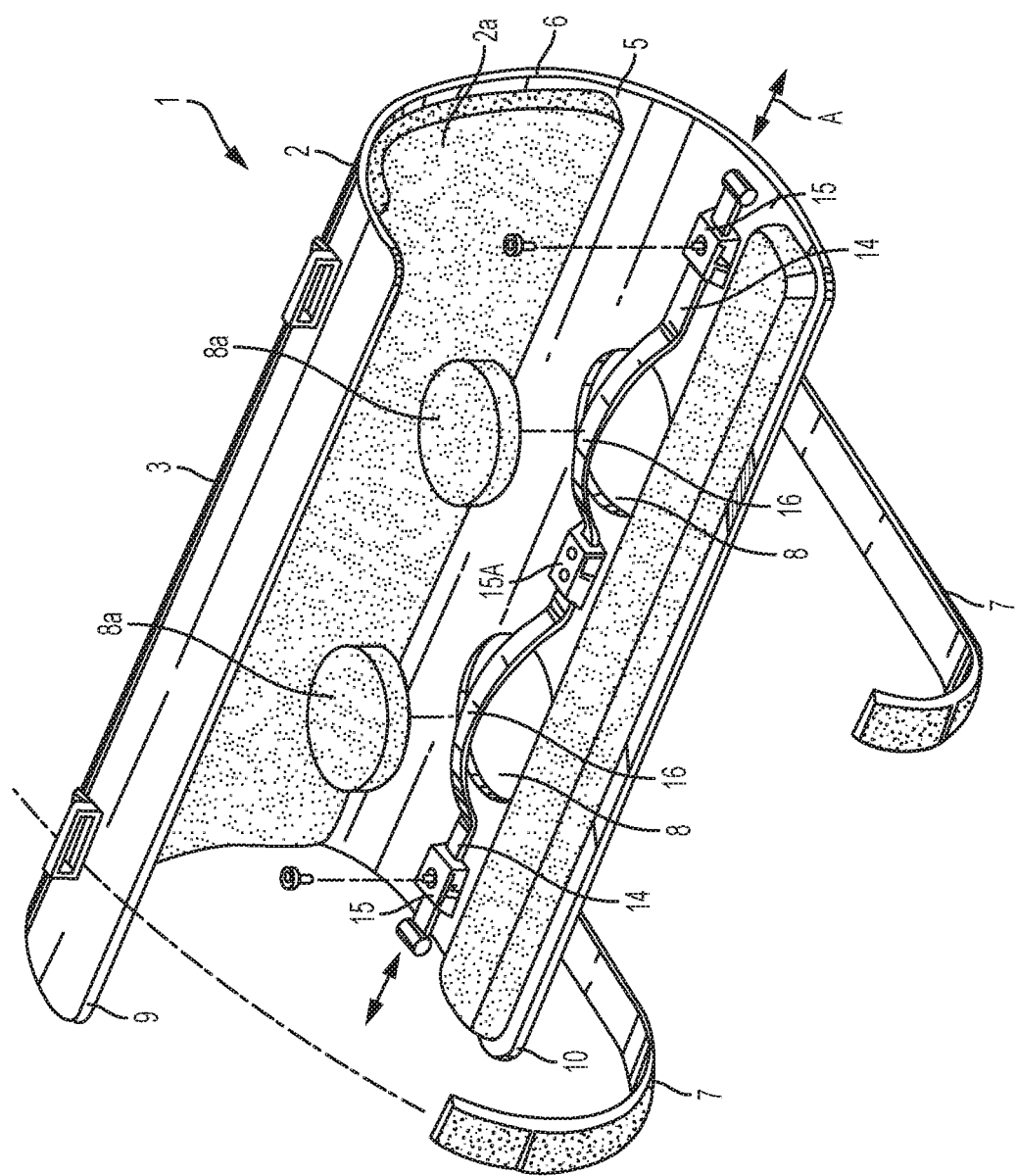
FIG. 5 shows an embodiment of the orthopaedic device in an exploded view with two access ports and two foam pads.

Turning now to FIG. 5, in a second variation of the orthopaedic device 1, the holder 2 may contain a plurality of access ports 8. The plurality of access ports 8 is particularly beneficial for positioning one or more pressure applying elements 16 onto soft tissue of the affected body part. In particular, the plurality of access ports 8 can permit the selective use and/or adjustment of one or more pressure-applying elements 16 at different locations of the holder 2 as shown in FIG. 7A where a pattern of access ports 8 are shown as disposed over the holder 2.

With multiple access ports 8 located along the holder 2, the healthcare professional may surround the arm with the holder 2 having the multiple access ports 8 and then use one or more pressure-applying elements 16 to apply pressure where the healthcare professional desires it.

Figure 7A:
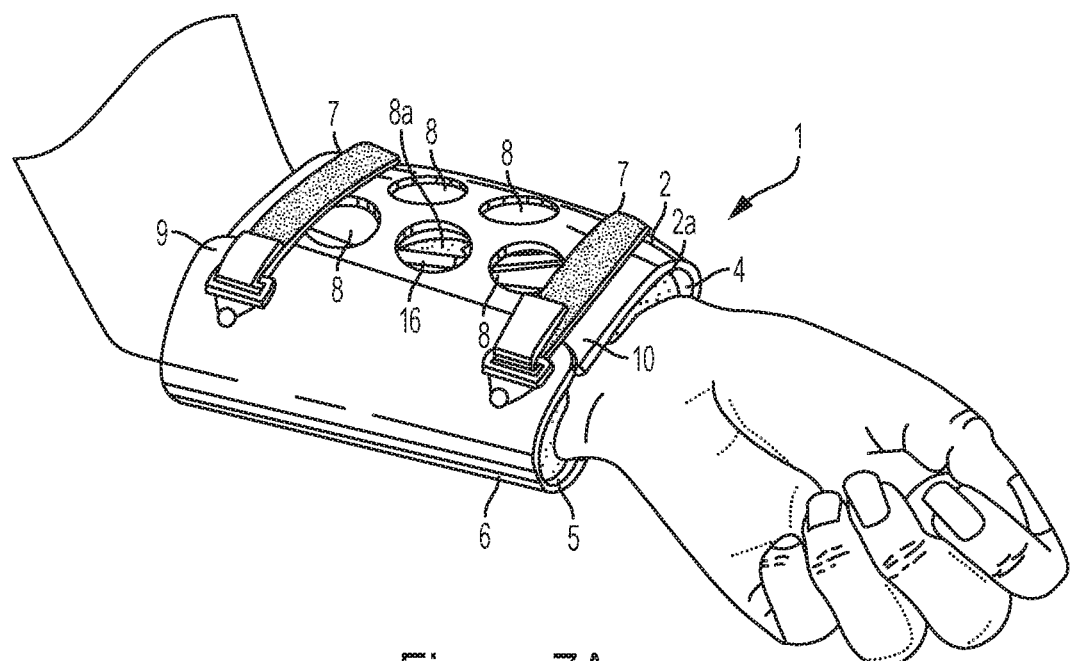
FIG. 7A shows an embodiment of the orthopaedic device with multiple access ports on the holder.

A uniform access port pattern such as the one shown in FIG. 7A is provided on the holder 2 to allow almost any soft tissue pressure application to be achieved by the use of appropriate pressure-applying elements 16. In this manner, the healthcare professional can have a holder 2 that includes multiple access ports 8 so the healthcare professional can first secure the holder 2 without requiring exact alignment of access ports 8 and use one or snore pressure applying elements 16 to achieve the desired pressure application pattern over the fracture area.

Figure 7B:
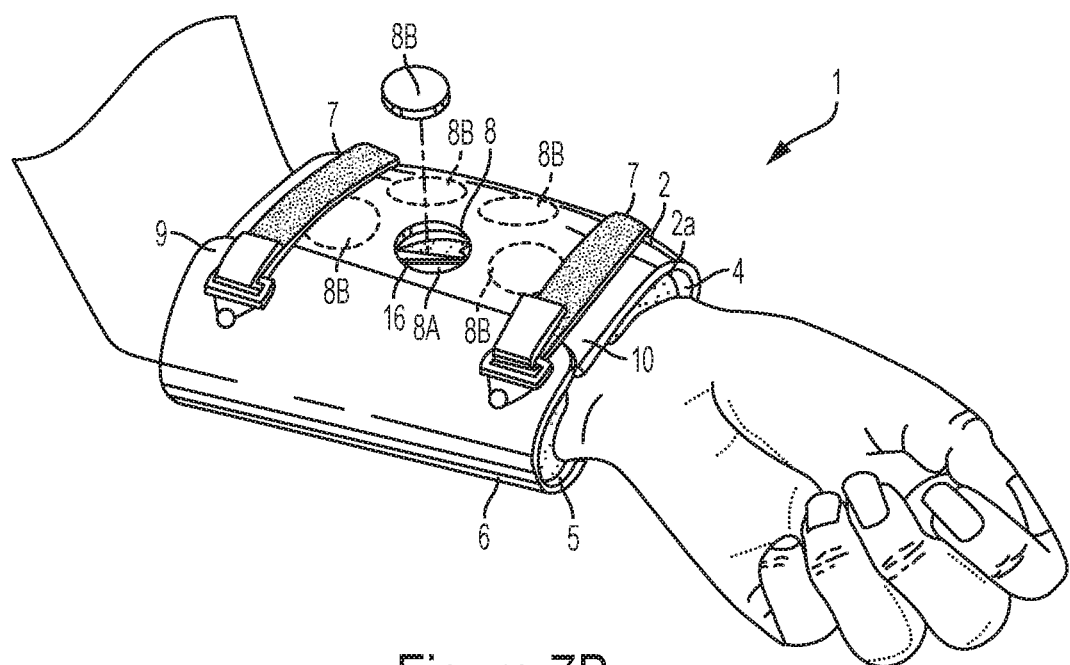
FIG. 7B shows an embodiment of the orthopaedic device with multiple covered access ports.

In FIG. 7A the access ports 8 are provided on the holder 2 in an opened configuration, however the present disclosure is not limited to this configuration, and the access ports 8 can be covered with a covering that is removable. In FIG. 7B, the provided access ports 8 are initially covered with removable coverings 8B. Accordingly, when the holder 2 is placed over the fracture, the healthcare professional may remove one of the coverings 8B to access the access port 8 beneath the covering 8B, and thus, introduce the pressure applying element 16 into the desired access port 8, and keep the remaining access ports 8 covered or closed.

In a third variation where a substantial amount of pressure is to be introduced over a specific portion of soft tissue, a group of pressure-applying elements 16 can be applied to extend into one access port 8 and to apply pressure to the particular portion of the soft tissue surrounding a bone fracture.

Figure 3:
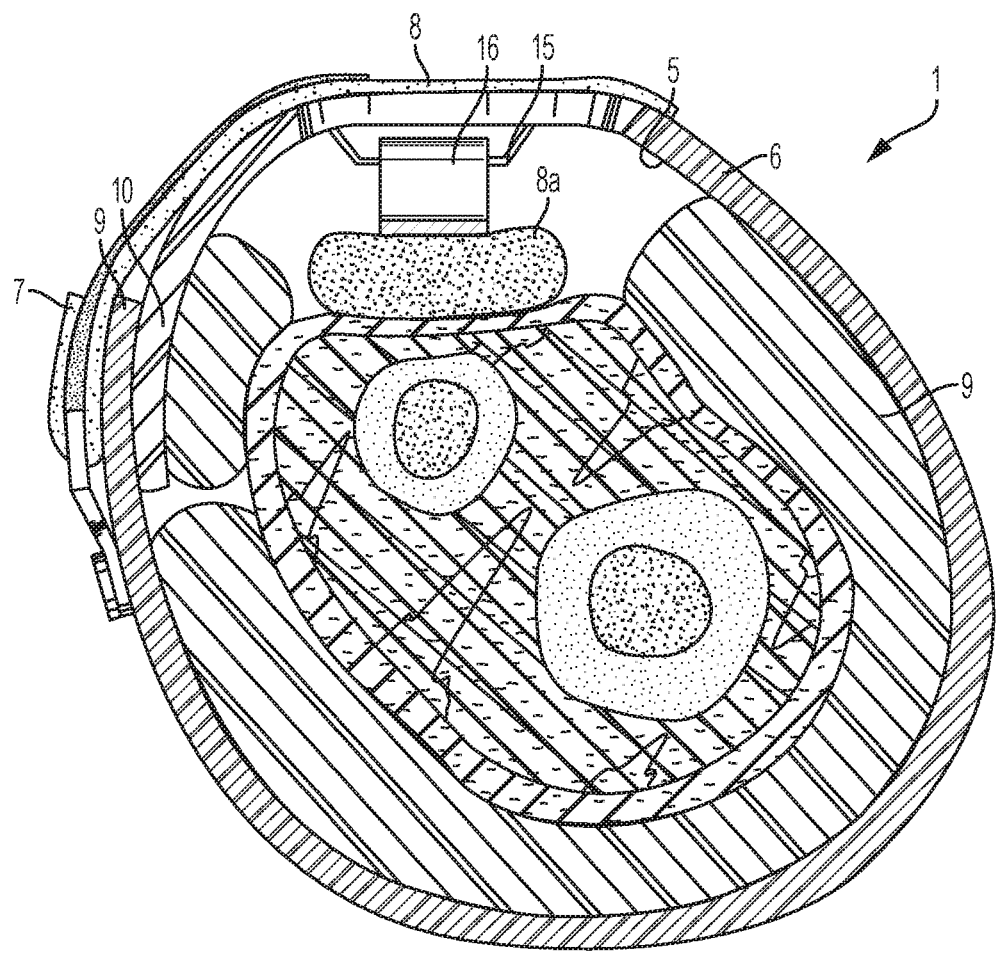
FIG. 3 shows a cross sectional view of the device of FIG. 1 applying pressure to the foam pad.

Turning now to FIG. 3, there is shown a cross sectional view of the orthopaedic device, and in particular, the pressure applying dement 16 applying pressure to an intermediary contact material 8a, through the access port 8, according to a fourth variation of the present embodiment. In the orthopaedic device 1, an intermediary contact material 8a can be used to transmit the pressure asserted by the pressure applying element 16, and to distribute the pressure such that the soft tissue is not injured. The intermediary contact material 8a, which is inserted between the pressure-applying device 16 and the soft tissue, can be either detachably engaged or permanently attached to the pressure applying element 16 or the holder 2. The intermediary contact material 8a has a size and a construction that renders the pressure applying element 16 capable of transmitting and distributing the applied pressure onto the soft tissue. The pressure distribution can be either nearly uniform or non-uniform on the contacting soft tissue surfaces.

The intermediary contact material 8a can be constructed in whole or at least in part for example, foam, a polyurethane, rubber, plastic, silicone, or any deformable material or any combinations thereof. Furthermore, the intermediary contact material 8a may also contain hollow compartments.

The intermediary contact material 8a can be, for example, a disc-like foam pad, as illustrated in FIGS. 2, 3 and 5. Alternatively, a foam inner lining 2a arranged to the inner surface of the holder 2 can serve as an intermediary contact material 8a to minimize direct contact of the hard shell structure of holder 2 with soft tissue and to distribute pressure applied by the pressure applying element 16 onto the soft tissue.

The thickness of intermediary contact material 8a can be, dependent on the material of construction, from a few millimeters to 1-2 cm or more. For example, generally, a thicker intermediary contact material is used with an orthopaedic device applied to a larger limb in order achieve the desired pressure distribution.

In a fifth variation, the pressure applying element 16 or the intermediary contact material 8a may include radiographic markers (i.e., a radiographically dense material) that can function as markers in an x-ray image in order to reveal the position and angle of the pressure applying element 16 relative to the bone fracture. X-ray images can be taken to determine the positioning of the pressure application area relative to the fracture. Appropriate adjustments can then be made to achieve proper positioning of the pressure application area.

It should be appreciated that the configuration of orthopaedic device 1 and, in particular, holder 2 may vary depending on, for example, the type, location and specific geometry of the bone fracture.

Method of Use

The orthopaedic device 1 described in the first and subsequent embodiments can be used in any suitable manner according to methods understood in the healthcare profession to align and treat bone fractures such that the healing of a bone fracture can be improved and in particular, accelerated.

There are many factors which can determine how the orthopaedic device 1 is used. Such factors include, for example, the type of fracture and the location of the fracture in the body. As an example, for an angulated fracture, the orthopaedic device 1 can be configured to selectively apply localized pressure against the apex of the angulation in order to reduce the angulation over time while promoting healing of the bone. In contrast, for a non-angulated type of fracture, for example, one fixed with an intramedullary rod, the orthopaedic device 1 can be configured to apply one or multiple points of localized pressure at the same time or alternated over time for the biochemical effects.

Figure 17:
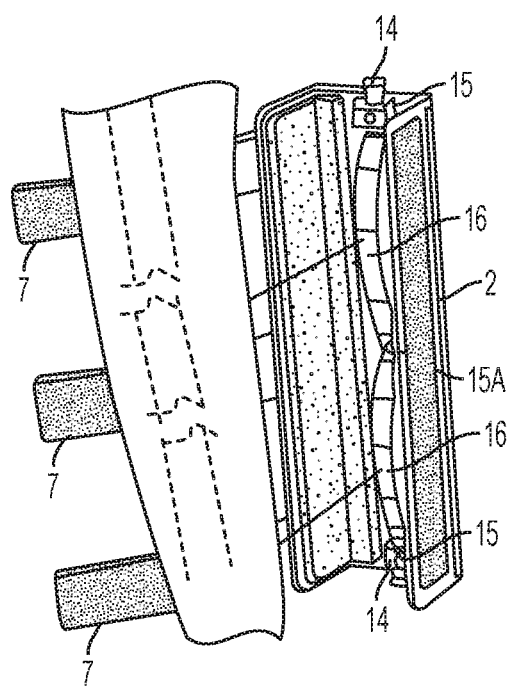

As illustrated in FIG. 17, the orthopaedic device 1 and, in particular, the holder 2 can be configured to treat a simple or segmental fractures (a single bone fractured in two different sites, simultaneously). The orthopaedic device 1, and in particular, the holder 2 can be configured to treat, for example, a complete fracture, incomplete fracture, linear fracture, transverse fracture, oblique fracture, segmental fracture, compression fracture, spiral fracture, stress fracture or other bone fractures with other geometry.

Figure 18:
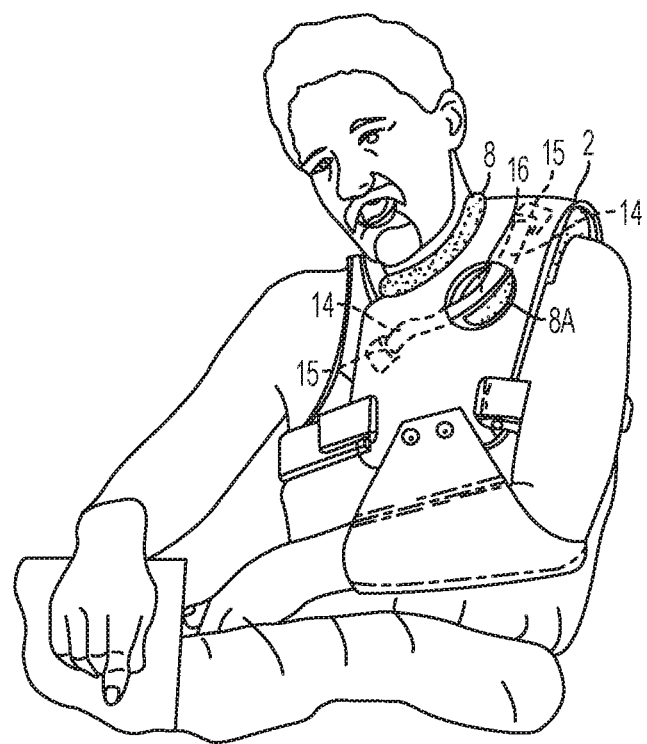

It should also be appreciated that the orthopaedic device 1 and, in particular, the holder 2 can be configured to be of a size suitable for encircling, in whole or in part, any body part. As illustrated in FIG. 18, the orthopaedic device 1 and, in particular, the holder 2 can be configured to encircle body parts such as the torso in order to treat bone fractures in those parts of the body. Other bones of the body which can be treated by orthopaedic device 1 include, for example, the humerus, radius, ulna, femur, tibia, fibula, clavicle, spine, pelvis, carpus, metacarpals, metatarsals, phalanx (for both hand and foot), talus, calcaneus, patella, scapula, sternum, and rib bones. In addition, the orthopaedic device 1 and, in particular, the holder 2 can be configured over the fractured part, to allow the pressure-applying element 16 to be positioned in proximity to and to treat fractures located on a diaphyseal, metaphyseal, proximal or distal portion of a bone. In FIG. 18, the holder 2 is applied to the shoulder and strapped to the chest wall fixing it over the fractured clavicle. The access port 8a is then positioned over the fractured clavicle, allowing the pressure-applying element 16 to be positioned over the fracture.

It should also be appreciated that the orthopaedic device 1 can be used in connection with other support structures.

The pressure applied by a pressure applying element 16 against soft tissue can be any quantifiable amount of pressure that can accelerate the healing of a bone fracture. For example, the applied pressure can be sufficient to diminish local blood flow and thereby increase the local free calcium ion concentration in the blood in soft tissues adjacent to the bone fracture. in a first example, the applied pressure is anywhere within the range of about 20 to about 100 mm Hg, and more typically within the range of about 30 mm Hg to about 90 mm Hg. In a second example, the applied pressure is within the range of about 30 to about 50 mm Hg. In a third example, the applied pressure is within the range of about 60 to about 90 mm Hg. In a fourth example, the applied pressure is within the range of about 30 to about 40 mm Hg. It should be appreciated that various applied pressure values/ranges and distributions are within the scope of the present disclosure and the present disclosure is not limited to any specific pressure value/range.

The period of time that the applied pressure is retained on the soft tissue may be as long as several days or may be very short, even less than 0.5 minute, applied intermittently, for example in a pulse-like manner. For example, the period of time can be the full period of time that the orthopaedic device 1 is worn by the user or a portion of time that the orthopaedic device 1 is worn. The present orthopaedic device 1 allows the amount of pressure and the intervals of applied pressure to be readily adjusted by the user.

Second Embodiment

In a second embodiment, an orthopaedic device 1 includes a holder 2 and a mechanical pressure applying element 16. The mechanical pressure applying element 16 is supported by and/or connected to the holder 2 and is configured to apply and maintain a desired pressure directly against the soft tissue or indirectly against the soft tissue through an intermediary contact material 8a.

FIG. 2 illustrates a first example of a mechanical pressure applying element 16 comprising a strip 14 that is relatively flexible but inextensible. The mechanical pressure applying element 16 further comprises locking/unlocking elements 15 disposed on the holder 2 at positions adjacent to the access port 8 such that a length-adjustable portion of strip 14 spans across the access port 8. The length-adjustable portion of strip 14 that spans across the access port 8 can be manipulated by the user into a convex shape in a direction toward the soft tissue to apply pressure to the soft tissue. The strip 14 can be arranged on the outer surface 6 of the holder 2 and be manipulated by the user to protrude through the access port 8 to apply pressure to the soft tissue. Alternatively, the strip 14 can be arranged on the inner surface 5 of the holder 2 allowing the user to manipulate the strip 14 through the access port 8. Both configurations facilitate the positioning of strip 14 and setting a desired pressure without disengaging the holder 2 from the soft tissue. Once a desired pressure is set, the strip 14 can be locked in place using locking/unlocking elements 15 to maintain the desired pressure for a desired period of time. The locking/unlocking elements 15 can also be unlocked in order to rapidly disengage the strip 14 in the event of discomfort, malfunction or emergency.

The strip 14 can be of any suitable thickness and constructed of any suitable material, which will permit the strip 14 to deform in bending and apply and maintain a desired pressure for a desired time interval. For example, the strips 14 can be constructed of a suitable metal or metal alloy, which contains enough rigidity to maintain a pressure against the soft tissue, while possessing enough flexibility to bend and bulge toward the soft tissue. Some examples of suitable metals include iron-containing metals (e.g., steel), titanium, aluminum and alloys. The strip 14 can also be constructed of, for example, a sufficiently flexible and inextensible plastic material or metal-plastic composite.

As illustrated in FIG. 5, in addition to the two locking/unlocking elements 15, the strip 14 may be fastened to holder 2 at one or more an additional points 15a. Such a configuration defines two length adjustable portions on the strip 14 that can be adjusted independently. Further, this configuration of strip 14 allows for selectively applying a localized pressure onto one or two regions of soft tissue by effectively bulging one or both length adjustable portions of the strip 14.

The strip 14 can be of a width which is less than or equal to or even larger than the diameter of the access port 8. Alternatively, two or more strips 14 can span across one or more access ports. Each of the multiple strips 14 can be individually and independently length-adjusted. Alternatively, the multiple strips 14 can be connected so that adjustment of one strip 14 can affect other strips 14. In such a configuration, the strips 14 are disposed in a parallel manner to form a width so that a smooth deforming surface (e.g., convex or biconvex) results.

Figure 4:
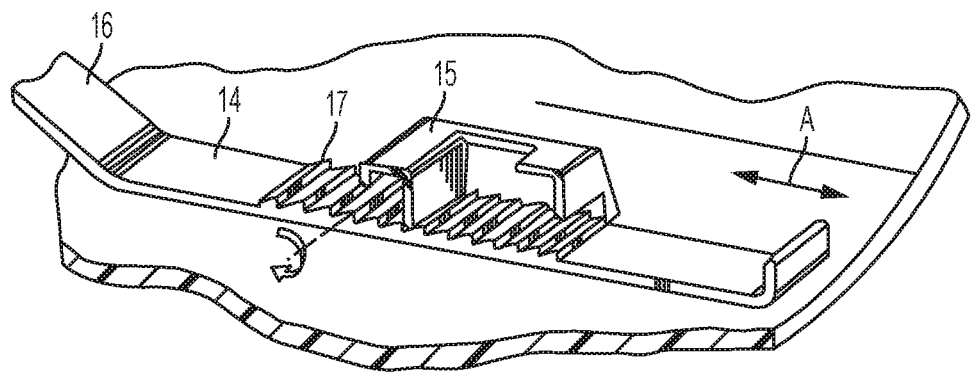
FIG. 4 shows a close up of a ratcheted strip.

In a second example, a mechanical pressure applying element 16 comprises a ratcheted strip 14, as illustrated in FIG. 4. The ratcheted strip 14 includes a number of ratcheting elements 17 that can be equally spaced from each other. The ratcheting elements 17 can be configured to engage with an interlocking receiving element 15 to secure the ratcheted strip 14 to apply a desired level of pressure to the soft tissue.

Figure 6:
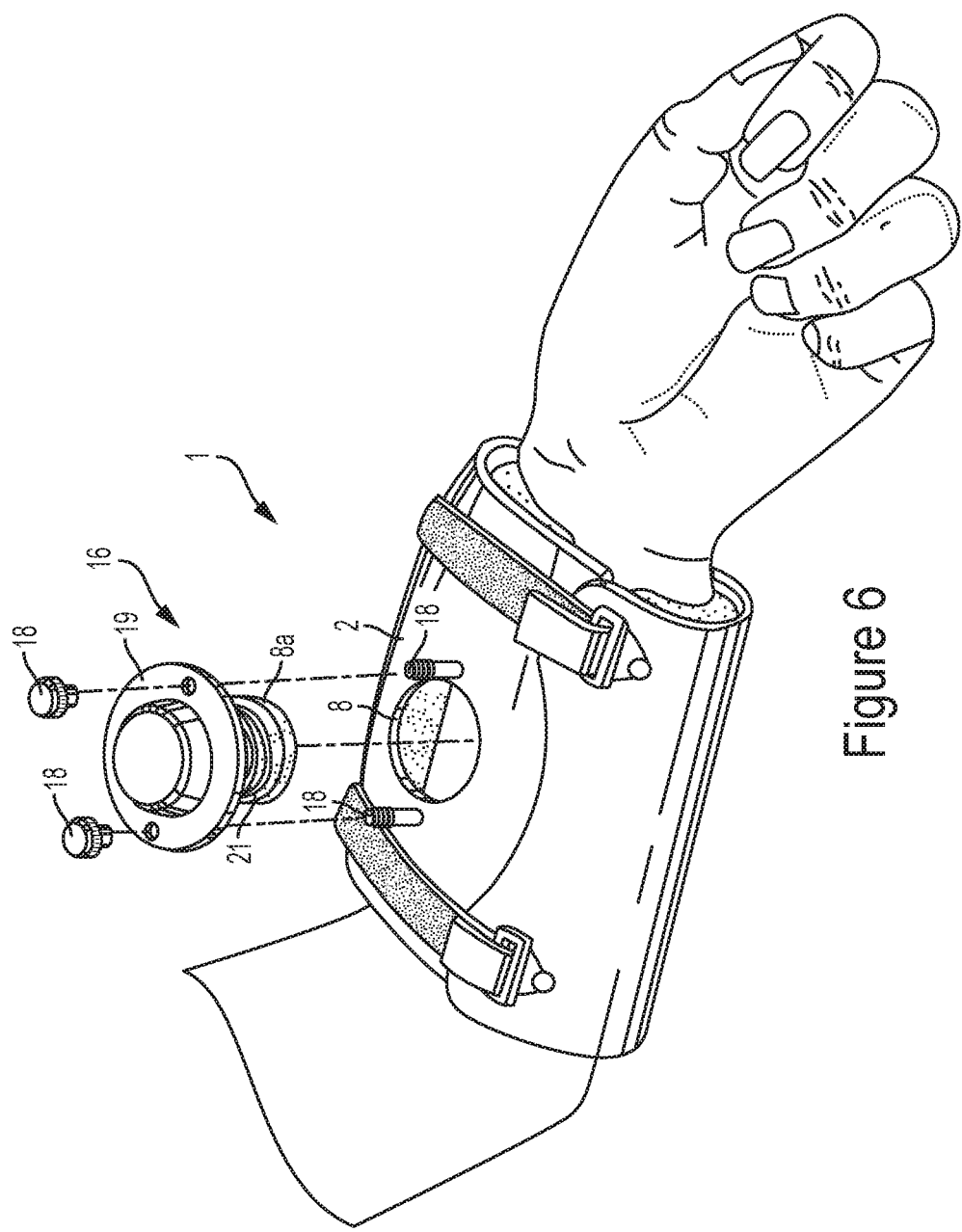
FIG. 6 shows an embodiment of the orthopaedic device including a spring-loaded mechanism for applying a localized pressure to soft tissue surrounding a fracture.

In a third example, a mechanical pressure applying element 16 comprises a load-adjustable spring element 21, which is operatively connected through an access port 8, between an intermediary contact material 8a, which further contacts the soft tissue, and a plate 19, which is located on another end of the load adjustable spring element 21 opposite from the intermediary contact material 8a, as illustrated in FIG. 6.

In FIG. 6, the plate 19 coupled to the load-adjustable spring element 21 is operatively connected to the holder 2 by a screw and nut mechanism 18 that can adjust the bias on the load-adjustable spring element 21. Tightening the nut of the mechanism 18 increases the load on the load-adjustable spring element 21. Loosening the nut of the mechanism 18 decreases the load onto the load-adjustable spring element 21. By increasing the load on the load-adjustable spring element 21, this spring state corresponds to an increased pressure on the soft tissue over the fracture, and decreasing the load on the load-adjustable spring element 21 corresponds to a decreased pressure on the soft tissue over the fracture. It should be appreciated that instead of a load-adjustable spring element 21, another deformable element may be used. Alternatively, the body of the mechanical pressure applying element 16 may be formed with threads and be screwed directly to the access hole 8 which is provided with matching threads to receive the element 16, thereby avoiding the need for the screw and nut mechanism 18.

The load-adjustable spring element 21 described above can also be operatively coupled to other pressure applying elements. For example, load-adjustable spring element 21 can be operatively coupled to a strip 14. By adjusting the screw and nut mechanism 18, the plate 19 can be moved to compress the load-adjustable spring element 21 against one or more strip 14 through an access port 8. When the desired pressure is attained, the strip 14 can be locked in place with locking/unlocking element 15 to maintain the applied pressure.

Figure 14:
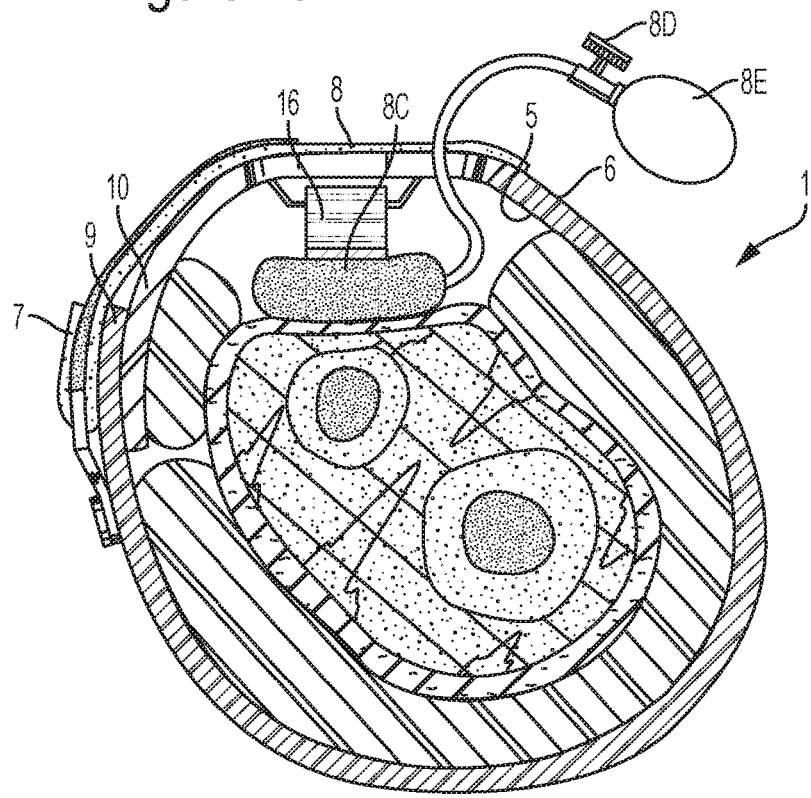

In a fourth example, the adjustable pressure applying element 16 comprises a bladder 8C containing a liquid, gas or a solidifiable As illustrated in FIG. 14, the bladder 8C can be connected to a valve 8D to introduce air (gas) or liquid via pump 8E, and can be supported with or connected to the inner surface 5 of the holder 2. The use of air (gas) in a relatively elastically expandable bladder 8C allows for the maintenance of a relatively uniform and constant pressure over the soft tissue. The bladder 8C can also be configured to be accessible through an access port 8. The fluid-filled bladder 8C is capable of being shaped, i.e., molded in form, through the access port 8 to protrude toward the soft tissue.

Figure 13:
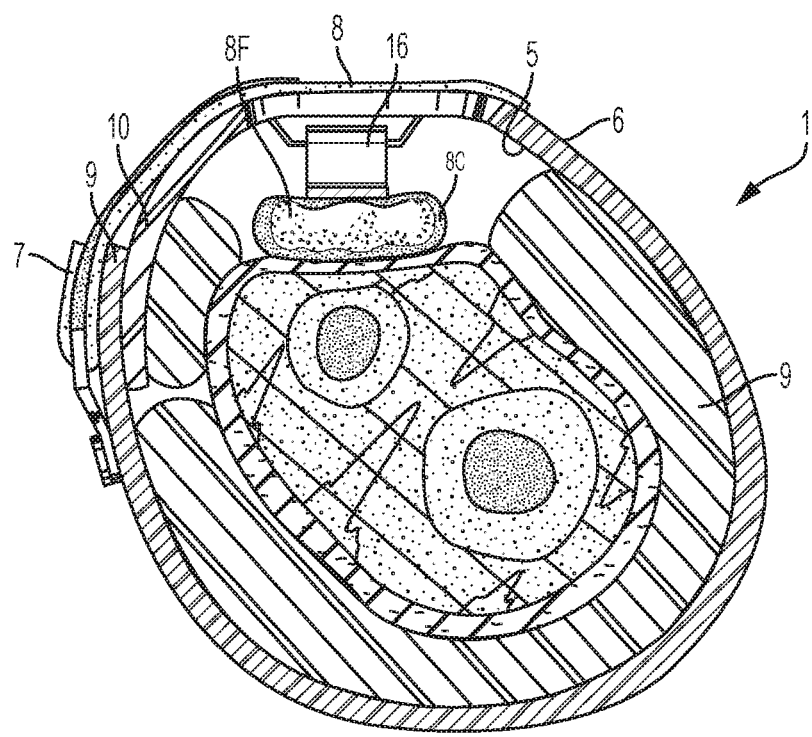
FIGS. 13 and 14 show cross sectional views of two embodiments of the orthopaedic device including adjustable fluid or gas filled bladders.

FIG. 13 shows a solidifiable liquid 8F introduced into bladder 8C. Upon establishing a desired pressure within bladder 8C against the soft tissue, the solidifiable liquid 8F is capable of changing into a rigid solidified form within a short period of time (e.g., in less than 1 minute).

The solidifiable liquid 8F can be any liquid known in the art capable of solidifying at room temperature in response to a stimulus. The stimulus can be, for example, a mixture of two portions of a mixture to commence a chemical reaction, which changes the solidifiable liquid 8F into a solid. The solidifiable liquid 8F should be capable of maintaining a rigid solid form either after removal of the stimulus or by intermittent or continued application of the stimulus. Alternatively, the stimulus can be an electrical charge or magnetic field supplied to a mixture to solidify the mixture.

The solidifiable liquid 8F can be, for example, a magnetorheological fluid. A magnetorheological (MR) fluid 8F is a type of fluid, which is converted to a highly viscous form or solid when stimulated by a magnetic field of appropriate strength. A MR fluid 8F is typically composed of micrometer or nanometer-sized magnetic particles (paramagnetic colloidal particles) suspended in a viscous medium, such as oil. The particles can be, for example, of an iron or magnetic iron oxide composition.

The disclosure also contemplates adjusting the magnetic field strength in order to vary the rigidity of the solidifiable fluid 8F in bladder 8C such that during exercise the pressure transmitted by the bladder 8C onto the soft tissue can be varied. Since a MR fluid requires the use of a magnetic field, the orthopaedic device 1 may also include a device in the holder 2 for providing a magnetic field. For example, appropriately sized electromagnetic coils can be included for this purpose.

Alternatively, the solidifiable liquid 8F can be an electrorheological fluid. An electrorheological (ER) fluid is a type of fluid which is converted to a highly viscous form or solid when stimulated by an electrical field (typically several kV/mm). An electrorheological fluid is typically composed of fine non-conducting (dielectric) particles (e.g., up to 50 microns in diameter) in an electrically insulating fluid. An example of an ER fluid 8F is corn flour suspended in an oil, such as a vegetable oil or silicone oil. The ER fluid 8F considered herein also include the more recent giant electrorheological (GER) fluids, which are typically able to sustain higher yield strengths at lower electrical fields. An example of a GER fluid 8F is a composition containing urea-coated nanoparticies of barium titanium oxalate suspended in silicone oil. The disclosure also contemplates adjusting the electric field strength in order to vary the rigidity of the solidifiable fluid 8F in bladder 8C such that during exercise the pressure transmitted by the bladder 8C onto the soft tissue can be varied. Since an ER fluid 8F requires the use of an electric field, the disclosure also contemplates including a device in the holder 2 for providing an electric field. For example, appropriately sized electrodes (charged plates) along with an electrical power source can be included for this purpose.

It should be appreciated that other mechanical pressure applying elements 16 can be used with the present disclosure. The above described embodiments are advantageous in that the pressure applied to the soft tissue can be adjusted and maintained without requiring removal or disengagement of the holder 2 from the body part.

Third Embodiment

A third embodiment is described below with reference to FIGS. 8-10.

Figure 8:
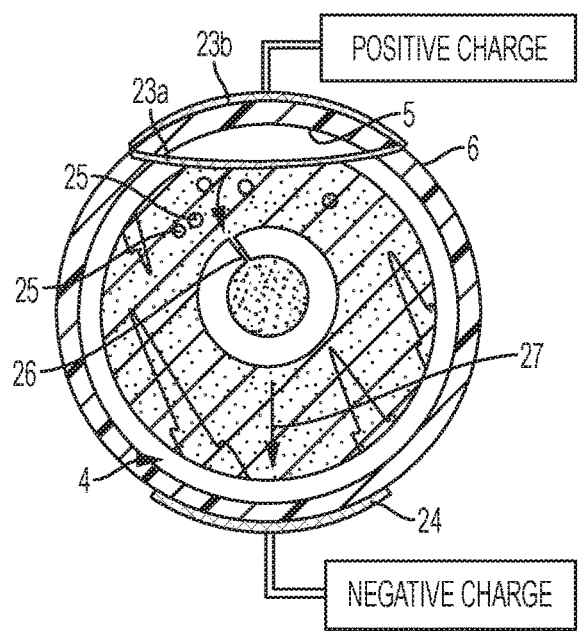
FIGS. 8-10 show three embodiments of the orthopaedic device containing capacitive coupling devices capable of applying two separate localized deforming pressure on soft tissue adjacent to a bone fracture.

FIG. 8 illustrates a cross-sectional view of an orthopaedic device 1 that includes a capacitive coupling device as a pressure applying element 16 for applying a soft tissue deforming pressure onto soft tissue adjacent to a bone fracture to treat and accelerate healing of the fracture.

The capacitive coupling device includes a first electrically-conductive foil element 23, having two foil portions 23a and 23b, and a second electrically-conductive foil element 24 that are positioned approximately opposite to each other on a holder 2. Foil elements 23 and 24 can be positioned or secured to the holder 2, for example, through access ports 8, such that a user can designate the positions of the foil elements 23, 24 on the holder 2 after the holder 2 is engaged to the soft tissue adjacent to the bone fracture.

The foil elements 23, 24 are electrodes and are designed such that foil elements 23, 24 can assume an electrical charge with portions 23a, 23b being positive and foil element 24 being negative.

The foil portions 23a and 23b are electrically interconnected to one another and contain the same charge. The foil portions 23a and 23b include a positive charge and thus repel from one another. The portion 23b is configured to be connected to the holder 2 to remain stationary, thereby allowing the portion 23a to repel away from portion 23b and to apply a pressure onto soft tissue when the portions 23a and 23b are charged.

The foil portion 23a can optionally contact an intermediary contact material to distribute the pressure applied by the foil portion 23 to the soft tissue adjacent to the bone fracture.

By modulating the electrical charge between the foil elements 23a and 23b, the amount of deflection of the foil portion 23a can be adjusted. Preferably, the foil portions 23a, 23b can be coupled to a controller (not shown) to permit the user to regulate the current passing through the foil portions 23a, 23b, and thus further adjust the amount of pressure on the fracture. For example, the controller can regulate the current passing through the foil portions 23a, 23b in an on-off pattern or other intermittent profile pattern of choice.

The foil portions 23a, 23h are constructed of any conductive material known in the art. Specifically, the foil portions 23a, 23h are constructed of resilient material which can apply and hold a suitable soft tissue deforming force on the fracture. Some examples of suitable materials for the foil portions 23a, 23b include various conductive metals (e.g., copper, silver, iron, and alloys or layered structures), and conductive polymers or plastics.

Figure 9:
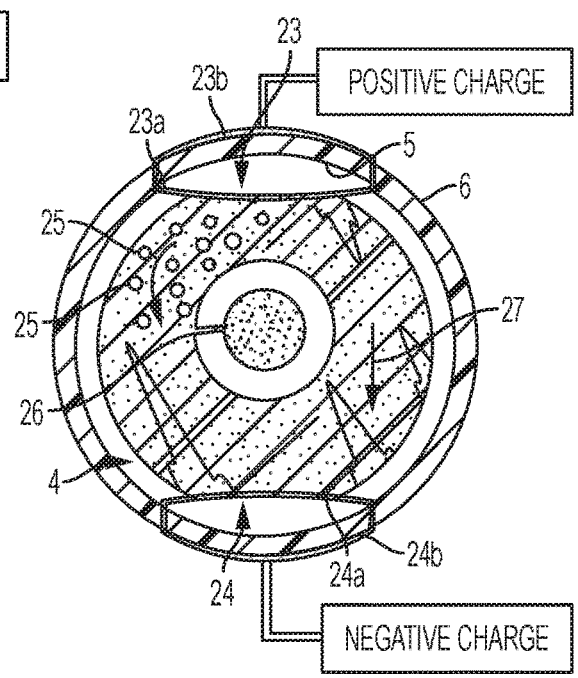

Alternatively, the foil portions 23a and 23b of like charge are not split from a common electrode as described in FIG. 8, but rather can be alternatively formed from two separate foil electrode 23a and 23b of like charge, with one foil electrode 23b attached to the inner surface 5 of the holder 2 and another electrode 23a being spaced away and in contact with the soft tissue and fracture to apply pressure to the fracture as shown in FIG. 9. The two separate foil electrodes 23a and 23b can be made to assume the same charge by, for example being connected to the same terminal of a battery, or by being connected to terminals of different batteries wherein the different terminals are of the same polarity.

The above described configuration of foil dements 23, 24 provides an additional benefit of directing calcium ions 25 toward the bone fracture by charge repulsion. In the above described configuration, an electrical potential 27 is created between foil elements 23, 24 such that calcium ions are directed away from the positive charged foil element 23 toward the negatively charged foil element 24. By positioning the deforming foil portion 23a against the fracture side of a bone, the calcium ions are directed toward, and thus concentrated at, the fracture site.

Turning now to FIG. 9, there is shown an alternative embodiment of the present disclosure wherein foil elements 23, 24 are positioned on a holder 2, with each foil element 23, 24 having two foil portions 23a, 23b, 24a, 24b, respectively. In this configuration, pressure can be applied at two regions of the soft tissue adjacent to the bone fracture from approximately opposite directions. This configuration may be advantageous in the instance whereby a fracture includes a specific geometry, and whereby the pressure and the electric field is applied to the body part from at least two different directions and can be adjusted to the desired level, independently.

Figure 10:
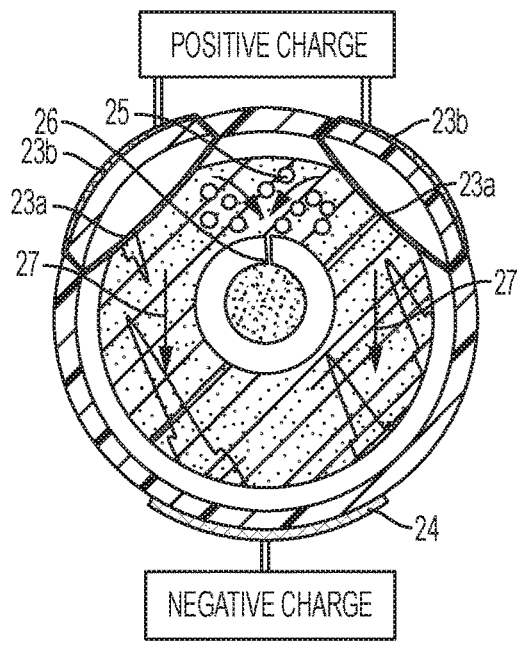

Turning now to FIG. 10, in an alternative variation, a plurality of positively charged foil elements 23, each having a pair of interconnected foil portions is arranged on a holder 2 relative to a negatively charged foil element 24. Such a configuration provides the orthopaedic device 1 with the ability to apply localized pressure simultaneously or alternately in at least two or more different locations of the soft tissue adjacent to the fracture for complex fracture shapes to accelerate healing of the fracture.

In another variation, the applied pressure can be modulated by the charge supplied to the desired foil elements 23a, 23b, 24, which modulates the field strength developed in the body part between the charged foil elements 23a, 23b, 24. For example, increasing a voltage between opposing foil elements 23a, 23b and 24 can increase the amount of applied pressure while decreasing a voltage between opposing foil elements 23a, 23b, and 24 can decrease the amount of applied pressure. Various amounts of charging can be supplied to the electrode foil elements and various charging configurations are possible and are within the scope of the present disclosure. Various charging patterns, including intermittent charging patterns, are therefore possible to apply to achieve various applied pressure levels and/or electric field strength levels and all such patterns are within the scope of the present disclosure.

The amount of voltage necessary to produce a sufficient level of charge in foil elements 23a, 23b, and 24 in order to produce a desired amount of localized pressure can all be readily calculated. For example, if the desired pressure (P) is known, the corresponding force (F) can be calculated by multiplying P by the area of contact of the contacting foil element 23a, 23b. Since is the sum of the repulsive force $F_1$ (i.e., between 23a and 23b) and the attractive force $F_2$ (i.e., between 23b and 24), $F_1$ and $F_2$ can be adjusted to arrive at the desired F. Coulomb's Law can be used to calculate the appropriate levels of charge required to adjust $F_1$ and $F_2$ in order to achieve a desired F. For example, by Coulomb's Law:

$F_1 = \frac{1}{4} \pi \varepsilon_0 (q_1 \times q_2 / r_{12}^2)$ for the repulsive force, wherein $r_{12}$ is the distance between diverted foil elements 23a and 23b, and $q_1$ and $q_2$ are the amounts of charge on each respective foil element 23a and 23b; and $F_2 = \frac{1}{4} \pi \varepsilon_0 (q_2 \times q_3 / r_{23}^2)$ for the attractive force, wherein $r_{23}$ is the distance between diverted foil elements 23b and 24, and $q_2$ and $q_3$ are the amounts of charge on each respective foil element 23b and 24.

Using the above equations, appropriate charging values $q_1$, $q_2$, and $q_3$ can be found in order to provide a force F that can provide a pressure P. The charging values can be realized by selection of an appropriate voltage, wherein the optimal voltage can be calculated. Alternatively, the voltage necessary to produce a given soft-tissue deforming pressure can be found experimentally by observing the amount of pressure applied per amount of voltage.

The orthopaedic device 1 can include any suitable device for applying a voltage onto the foil elements 23a, 23b and 24. For example, the orthopaedic device can include a suitable electrical charging device, such as provided by a lithium-ion rechargeable battery, a plug in electrical connection, a nickel hydride battery, a renewable source, like a solar cell or another electrical source, such as a small electrical generator with a stator and rotor. The orthopaedic device 1 can also include battery connection ports and conductive leads (not shown).

Fourth Embodiment

A fourth embodiment of orthopaedic device 1 comprising a holder 2 and a magnetic device as pressure applying element 16 connected to the holder 2 for applying a soft-tissue deforming pressure onto soft tissue adjacent to a bone fracture is described below with reference to FIG. 11.

The magnetic device includes a magnetic source 28 operating (e.g., attached) on a first side of the holder 2 and a flexible permanent magnetic strip element 29 associated with the magnetic source 28 positioned through an access port onto the holder 2.

In one configuration, the magnetic source 28 is an electromagnetic coil coupled to a power supply. The magnetic source 28 is capable of producing an adjustable magnetic field by modulation of the applied current to the electromagnetic coil. The flexible permanent magnetic strip element 29 is positioned through an access port on to the holder 2 and is operatively connected, for example, to the inner surface 5 of the holder 2 such that at least a portion of the permanent magnetic strip element 29 can protrude toward and apply pressure to a region of the soft tissue adjacent to the bone fracture when the magnetic source 28 is activated. The flexible permanent magnetic strip element 29 can be attracted or repulsed toward the soft tissue by inducing a magnetic field from the magnetic source 28, which can be the same polarity as the side of the flexible permanent magnetic strip element 29 facing the magnetic source 28. The like magnetic polarities may repel each other and cause the flexible permanent magnetic strip element 29 to protrude toward the body part, or alternatively, the opposite magnetic polarities can cause the flexible permanent magnetic strip 29 to move away from the fracture to reduce the applied pressure to the soft tissues surrounding the fracture.

It should be appreciated that an intermediary contact material (ex. foam pad 8a) can be positioned between the soft tissue and the flexible permanent magnetic strip 29 to distribute force to the soft tissue.

The flexible permanent magnetic strip 29 is constructed of any material, which is permanently magnetic, and of a suitable resilient construction (including thickness and composition) which renders the flexible permanent magnetic strip 29 capable of applying and holding a suitable soft-tissue deforming force. Some examples of suitable materials for the magnetic strip 29 includes any of the magnetic compositions known in the art (e.g., magnetite, cobalt, nickel, ceramic magnets, alnico, ticonal, rare earth magnets (e.g. samarium-cobalt and neodymium-iron-boron (NIB) magnets), combinations thereof, coatings thereof, and layered and non-layered composites thereof.

Figure 12:
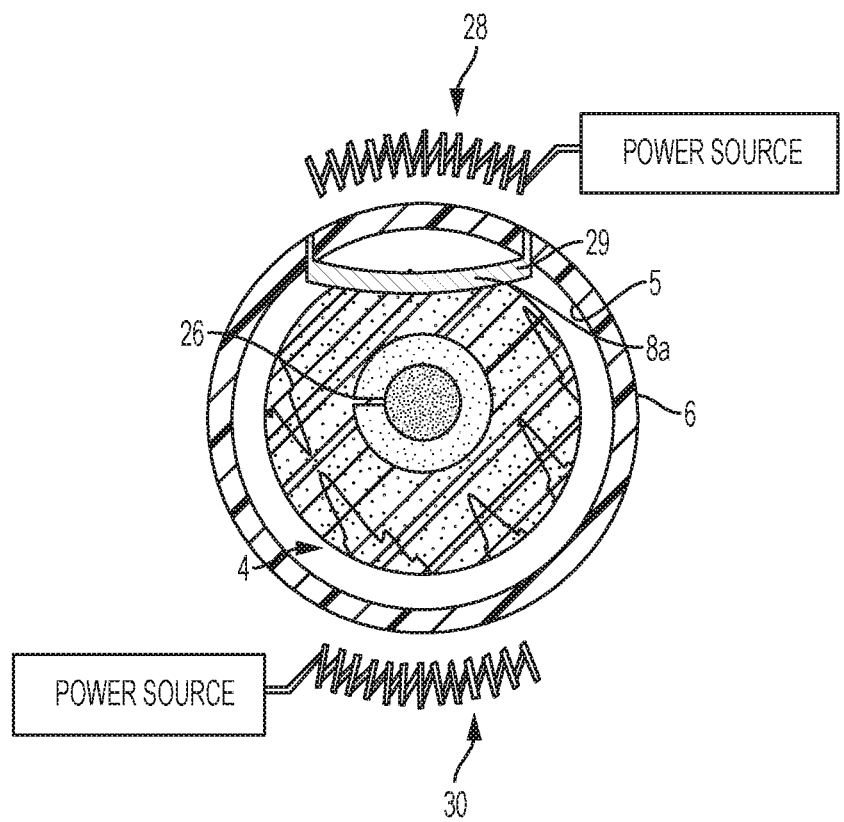

Turning now to FIG. 12, there is shown an alternative configuration with at least two magnetic sources 28, 30 to manipulate and adjust the amount of pressure the flexible permanent magnetic strip 29 applies to the soft tissue adjacent to the bone fracture. The second magnetic source 30 is disposed substantially opposite the first magnetic source 28. It should be appreciated that this positioning is illustrative and may change depending on the orientation of the fracture. The second magnetic source 30 operates on a second side of the holder 2 and approximately opposite to the first side; however, the magnetic sources 28 and 30 may be placed in any desired location relative to the fracture. Each of the first and second magnetic sources 28 and 30 produce magnetic fields. The two magnetic sources 28 and 30 work together to promote the bulging of the flexible magnetic strip 29 to apply pressure to the soft tissue and the fracture. Specifically, the switchable magnetic source 28 repels the flexible magnetic strip 29, while the switchable magnetic source 30 attracts the flexible magnetic strip 29.

Figure 11:
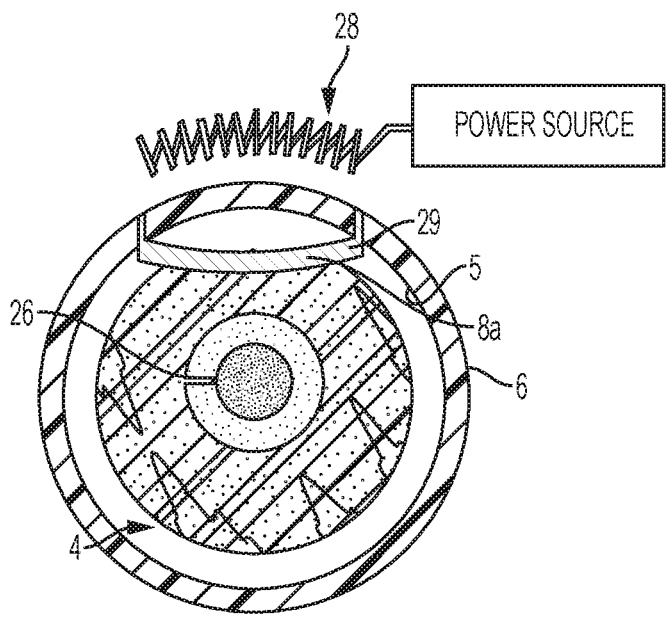
FIGS. 11 and 12 show two embodiments of the orthopaedic device containing magnetic coupling devices capable of applying a localized deforming pressure on soft tissue adjacent to a bone fracture.

It should be appreciated that the orthopaedic device 1 is not limited to a single magnetic strip 29 as show in FIGS. 11 and 12, and may have at least two strips 29. The number of magnetic strips 29 may depend on the fracture and geometry of the fracture. it should also be appreciated that the magnetic strip 29 is not limiting to one bending or bulging curved portion that contacts the tissue but depending on the polarity, the magnetic strip 29 can have more than one bulging or more than one curved surface. For example, a magnetic strip 29 can be connected to the concave inner surface 5 of the holder 2 in more than two locations such that more than one bulging section on the strip 29 can result. The holder 2 can apply localized pressure simultaneously or in different locations of the body part adjacent to the fracture to accelerate the healing. For example, the pressure can be adjusted by the selective operation of the magnetic sources 28, 30 by modulating the magnetic field or the current supplied to the coil.

The applied pressure is modulated by the magnetic field strength applied onto the flexible magnetic strip 29. For example, increasing the magnetic field strength can increase the amount of applied pressure, while decreasing the magnetic field strength can decrease the amount of applied pressure. The intensity of the magnetic field necessary to produce a sufficient attractive/repulsive force between the desired coil 28 or 30 and the magnetic strip 29 can be changed to produce a desired amount of pressure. Various magnetic field strength patterns, including intermittent charging patterns, are therefore possible to apply to achieve various applied pressure levels and/or magnetic field strength levels and are within the scope of the present disclosure.

A benefit of the magnetic field produced by the sources 28 or 30 is the ability to favorably influence calcium ions at the fracture site. For example, a magnetic field will concentrate the calcium ions in the compressed region because they are deflected by the magnetic field toward the fracture site. Such a magnetic field causes the calcium ions flowing in blood vessels near the fracture to follow circular paths of radius $r=mv/qB$, where m is the mass of the calcium ion, V is its velocity, q is its charge, and B is the applied magnetic field. By manipulating the intensity of the magnetic field, the trajectory of the calcium ions can be manipulated to congregate in the blood vessels surrounding the fracture. Because the flexible magnetic strip element 29 is intimate with soft tissues over the fracture, this effect is maximized. This increased concentration of calcium ions will further accelerate healing of the fracture.

The amount of magnetic field strength necessary to produce a suitable deforming force may depend on the size and construction of the flexible magnetic strip 29 as well as other factors. For example, if the desired pressure (P) is known, the corresponding force (F) can be calculated by multiplying P by the area of contact of the flexible magnetic strip 29. Since F is the sum of the repulsive force $F_1$ (i.e., between 28 and 29) and the attractive force $F_2$ (i.e., between 29 and 30), $F_1$ and $F_2$ can be adjusted to arrive at the desired F. To calculate the appropriate magnetic field required to adjust $F_1$ and $F_2$ in order to achieve a desired F, the equation $F=A*B^2/2*\mu°$ can be used, wherein F is force in Newtons, A is the surface area of the mat and coil in meter$^2$, B is the strength of the magnetic field in weber/meter$^2$, and $\mu°$ is the magnetic permeability constant. For example, to apply about 30 mm Hg pressure (about 400 dyne/cm) to the soft tissues by a 10 cm by 10 cm magnetic strip 29, a magnetic field of 0.01 weber/meter$^2$ (i.e., approximately 100 Gauss) can be used. When there is separation of the magnet source of length L by distance x, the Force F can be represented as $F=B^2*A^2(L^2+R^2)/\pi\mu°L^2[1/x^2-1/(x+2L)^2-2/(x+L)^2]$ wherein R is the radius of the magnet or coil 28. Various coil 28, 30 and magnetic strip 29 size configurations are possible and within the scope of the present disclosure.

The orthopaedic device 1 can include a suitable electrical power supply for creating a magnetic field in the electromagnetic coils 28 and 30. For example, the orthopaedic device 1 can include a battery or other electrical source for this purpose, such as a photovoltaic solar cell, a capacitor, an ultra-capacitor, a lithium ion battery, a nickel hydride battery, an electric generator including a rotor and a stator or a plug for coupling the electromagnetic coils 28 and 30 to an electrical household power supply line.

The orthopaedic device 1 can also include features (not shown) for connecting the power supply with the holder 2 and the magnetic device 28 and 30. In one configuration, at least one of the magnetic sources 28 and 30 and the permanent magnetic strip element 29 are detachably engaged with the holder 2 using a suitable detachable connector, such as, a clip, a removable connector engaged in an engageable slot or groove located in or on the holder 2. In another configuration, at least one of the magnetic sources 28 and 30, and the permanent magnetic strip element 29 can be fixedly attached to the holder 2. An intermediary contact material can be connected to the permanent magnetic strip element 29 or may be placed between the soft tissue and the permanent magnetic strip element 29 to distribute the pressure along the soft tissue and fracture to accelerate the healing.

Fifth Embodiment

The holder 2 may further include a pressure indicator to provide a quantifiable indication of the pressure being applied to the soft tissue and the fracture. The pressure indicator (not shown) may provide an indication to a user that a suitable pressure has been achieved to accelerate the healing of the fracture or when a desired pressure against soft tissue has been reached, or alternatively that the pressure should be increased/reduced.

In one configuration of the pressure indicator, an auditory indicator can sound to indicate that the desired pressure has been reached.

In another configuration of the pressure indicator, a visual-based indicator can display, for example, numbers, colors, or both, to indicate a certain degree of applied pressure. The visual-based indicator is based on a mechanism whereby as the strip 14 is pressed down to exert pressure to the surface of the body the force exerted on the locking ends 15 would be utilized to indicate the pressure applied to the body surface. This can be accomplished, for example, by attaching at least one of the locking ends to the holder 2 by a relatively stiff spring. The extension/contraction of the spring will then indicate the amount of force being transferred to the holder 2, thereby the pressure exerted to the body surface. A coloring or marking means can also be used as a scale to indicate the level of pressure applied to the body surface.

In another configuration, a similar type of mechanism is applied to a spring element 21 described above with regard to FIG. 6, wherein a flexible strip with pressure-indicating marks is overlaid onto or connected to the spring element 21. The compression and expansion of the spring element 21 causes the pressure-indicating flexible strip (not shown) to move in a like manner. A pressure-indicating mark on the flexible strip, when visible, thus indicates the applied pressure for a given compression of the spring element 21.

In yet another configuration, the visual-based indicator can operate by use of a material or combination of materials, which exhibit a change in color when a pressure change occurs. Various indicator configurations are possible and within the scope of the present disclosure.

Sixth Embodiment

Figure 19:
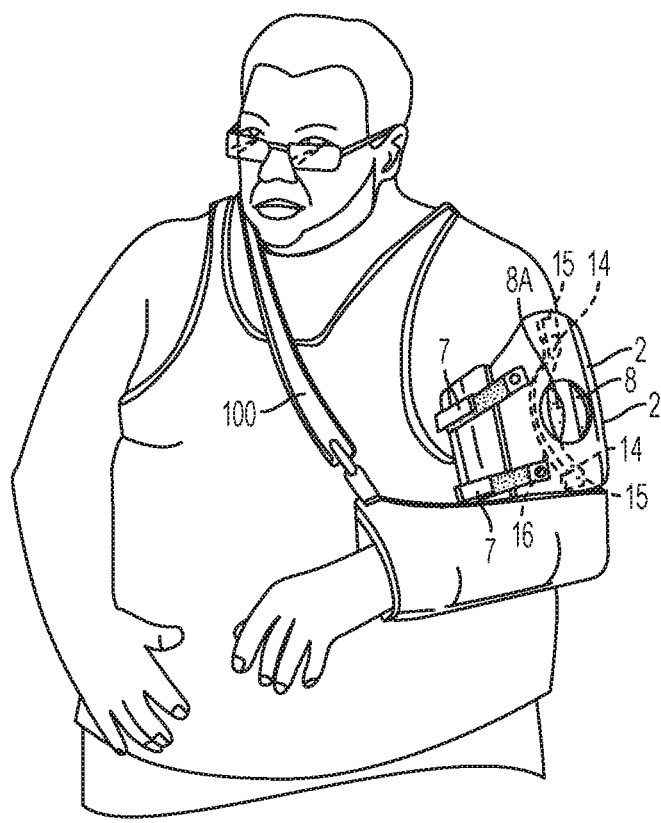
FIGS. 19 and 20 show an embodiment of the orthopaedic device for positioning and maintaining a localized pressure over a bone fracture in an obese patient.
Figure 20:
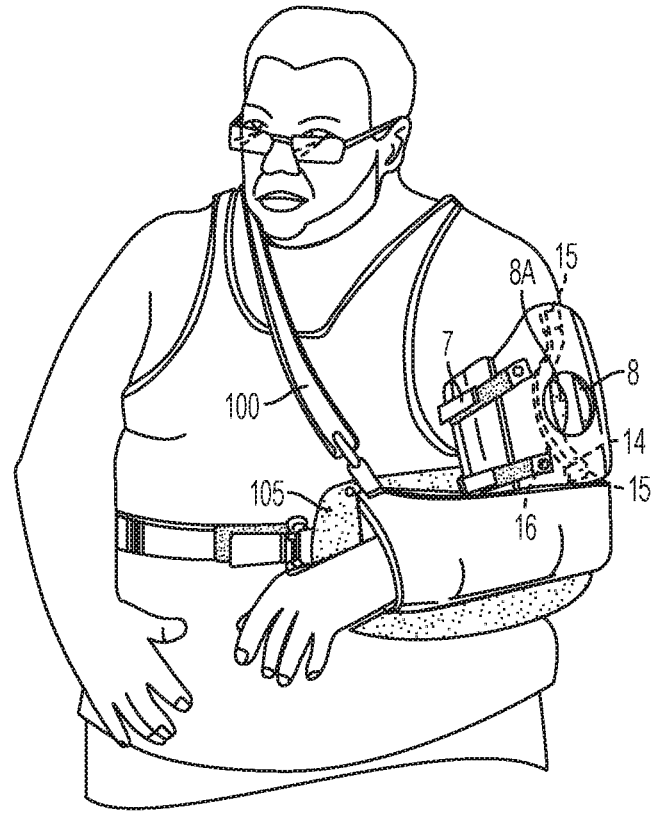

A sixth embodiment is described below with reference to FIGS. 19 and 20.

In the particular case of a morbidly obese patient, a special arrangement may be necessary to keep a localized pressure in place over a fracture since the weight of a limb or other body part may interfere with positioning of holder 2 (e.g., a brace or sling). A fracture of this type in an obese patient can be difficult to control with a single positioning device, such as a holder 2. A holder 2 alone typically cannot generate enough force to overcome the weight of the limb distal to the fracture. The use of an additional positioning device, such as a sling 100 or a pillow 105, is often helpful.

For example, in some morbidly obese patients, a humeral fracture can angulate over the torso, particularly when the fracture is in its mid-third and is unstable, i.e., transverse. In one configuration, as depicted in FIG. 19, this particular situation can be remedied by using a holder 2 (preferably, a BIO-CHEM BRACE) in the upper extremity in combination with an additional shoulder sling 100 for further support. In addition, an abdominal pillow 105 can be attached to the sling 100 to maintain the elbow away from the torso, as also shown in FIG. 20. Together, the holder 2 and the sling 100 together can supply the forces needed to maintain the localized pressure over the fracture.

Seventh Embodiment

An intermediate contact material such as 8A in FIG. 2 of the appropriate size, shape, thickness and density can be inserted above or below the electrical foil 23A in FIGS. 8-10 to achieve the desired pressure. This may require the holder 2 to be disengaged.

It is appreciated that the foil 23A may be used to apply the electric field without need for charged foil elements 23b or 24. This embodiment allows different application schedules for the mechanical applied pressure, electrically applied pressure and the electric field.

Eighth Embodiment

An intermediate contact material such as 8A in FIG. 2 of the appropriate size, shape, thickness and density can be inserted above or below the flexible permanent magnetic strip element 29 in FIGS. 11-12 to achieve the desired pressure. This may require the holder 2 to be disengaged.

It is appreciated that the flexible permanent magnetic strip element 29 may be used to apply the magnetic field without the need for magnetic source elements 28 and 30. This embodiment allows different application schedules for the mechanical applied pressure, magnetically applied pressure and the magnetic field.

Ninth Embodiment

An intermediate contact material such as 8A in FIG. 2 of the appropriate size, shape, thickness and density can be inserted above or below the electrical foil 23A and the flexible permanent magnetic strip element 29, to achieve the desired pressure. This may require the holder 2 to be disengaged.

It is appreciated that the electrical foil 23A and the flexible permanent magnetic strip element 29 may be used to apply both an electric and magnetic field without the need for charged foil elements 23b or 24 or the magnetic source elements 28 and 30. This embodiment allows different application schedules for the mechanical applied pressure, electrically and magnetically applied pressure and electrical and magnetic field.

Numerous modifications and variations of the present invention are possible in light of the above teachings without departing from the spirit or scope of the invention. It is therefore to be understood that within the scope of the appended claims, the invention may be practiced otherwise than as specifically described herein.

FIGS. 21 to 24 relate to the application of the device and method of use for treating bone fractures disclosed in the patent to the treatment of cases employing "Distraction Osteogenesis" and the like in which external fixators are used.

Distraction Osteogenesis is used for fracture management, lengthening, compression, deformity correction, angular correction, limb reconstruction and the like. External devices of different type are used for distraction Osteogenesis. The most common such devices are the so-called "ring fixators" and "rail (lengtheners) fixators". These devices, hereinafter referred to collectively as "external fixators", generally consist of attaching at least two sets of elements such as pins, screws or wires to the bone on either side of the fracture or subperiosteal osteotomy, and attaching externally positioned rigid but adjustable mechanisms to affect the desired level of distraction, compression, angular rotation, etc., between the said bone segments on either side of the fracture or subperiosteal osteotomy.

Figure 21:
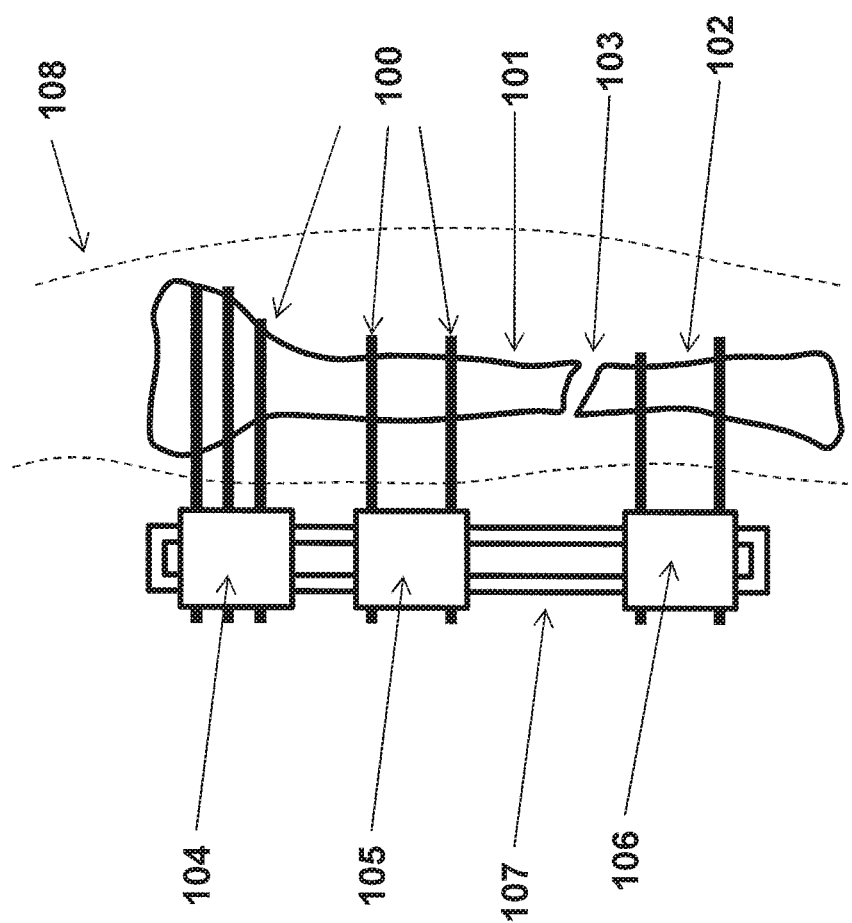
FIGS. 21-24 illustrate embodiments of rail type external fixator orthopaedic devices and ring type external fixator orthopaedic devices.

In FIG. 21 and the schematics of such basic rail type and ring type external fixators are shown, respectively, as attached to a long bone subperiosteal osteotomy site.

As can be seen in the schematic of FIG. 21, a rail type external fixator generally consists of a number of groups of mostly two or three screws 100 (in FIG. 21 three such groups are shown) that are attached to both side 101 and 102 of the bone fracture or subperiosteal osteotomy 103. The blocks 104, 105 and 106 are attached to each of the aforementioned three groups of screws. The three blocks 104, 105 and 106 are in turn attached to the "rail" 107 using means such as clamping with tightening screws, with the location of each along the length of the rail being adjustable. Provisions are also provided in certain such block designs to allow their orientation relative to the rail to be also adjustable directly or through the use of certain attachment mechanisms that are not shown in this illustration. After the screws 100 have been installed and the blocks 104-106 have been assembled onto the rail 107, the surgeon can then adjust the relative position of the blocks 104-106 on the rail to achieve the desired level of distraction (or compression or angular rotation) between the bone segments 101 and 102 outside the limb 108.

Figure 22:
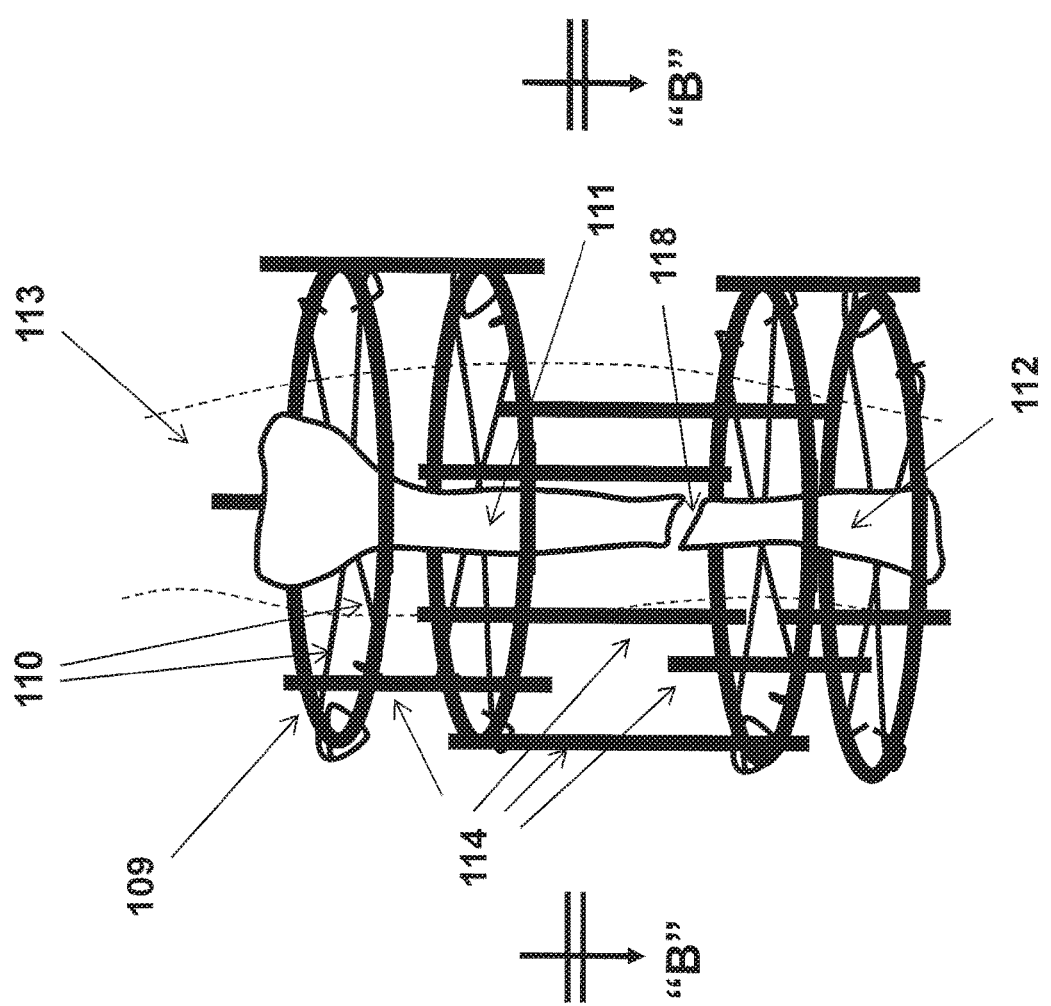

The ring type fixators, a schematic of one which is shown in FIG. 22, perform the same basic function as the aforementioned rail type fixators. These fixators usually use transfixion wires 110 and external fixation pins attached to rings 109 that encircle the affected limb 113. These rings are then attached to each other at several locations around the rings with components such as threaded rods and nuts 114 to create a relatively rigid frame. In the schematic of FIG. 22 four such rings 109 are shown. The transfixion wires 110 which are passed through the bone segments 111 and 112 of the limb 113 at the level of each ring and are attached to the rings. The rings may be complete or in segments that are attached to each other, e.g., by bolts. The transfixion wires 110 are attached to the ring using different methods such as by the use of bolt and nuts. Usually each pair of adjacent rings 109 is attached to each other with at least three threaded rods 114 with a pair of nuts (not shown) at each attachment point to achieve a rigid but adjustable attachment to the rings 109. At least one but preferably two such ring needs to be used on either side of the fracture or subperiosteal osteotomy site 118. The lengths of each threaded rod 114 is then adjusted to achieve the desired level of distraction (or compression or angular rotation) between the bone segments 111 and 112 outside the limb 113.

Ring fixators are most commonly applied to the tibia, but can also be applied to the femur, the humerus, the foot, the hand and the forearm.

Distraction Osteogenesis for fracture management, lengthening, deformity correction, angular correction, limb reconstruction, and other similar procedures is a prolonged process. For example, the procedure to elongate tibia in humans may take up to six or more months to allow for the bone formation to fill in the gap. A need therefore exists for the development of methods and related devices that could be used to speed up this process.

In the embodiments of FIGS. 1-3, 5-6, 7A and 7B and 13-20, certain holder (such as holder 2 in the embodiments of FIGS. 1-3, 7A, 7B and 15-8) is configured to be positioned onto a target body part and to engage soft tissue adjacent to a bone fracture. It is also understood that although the holders are illustrated in the figures as a brace, the holders may alternatively be a splint, a cast, a bandage, or a structural member that surrounds a body part, in whole or in part. The one or more pressure applying elements (element 16 in the embodiments of FIGS. 1-3, 7A, 7B and 15-8) as was earlier described in detail below are then configured to be adjustably positioned on to the holder and configured to adjustably apply pressure to the soft tissue adjacent to the bone fracture.

In the following embodiments of the present invention, the external structure of the "rail fixators" and "ring fixators" shown in FIGS. 21 and 22, respectively, are used in place of such holders to attach appropriate components to be described below that are configured to similarly and adjustably apply pressure to the soft tissue adjacent to the bone fracture or subperiosteal. osteotomy.

Figure 23:
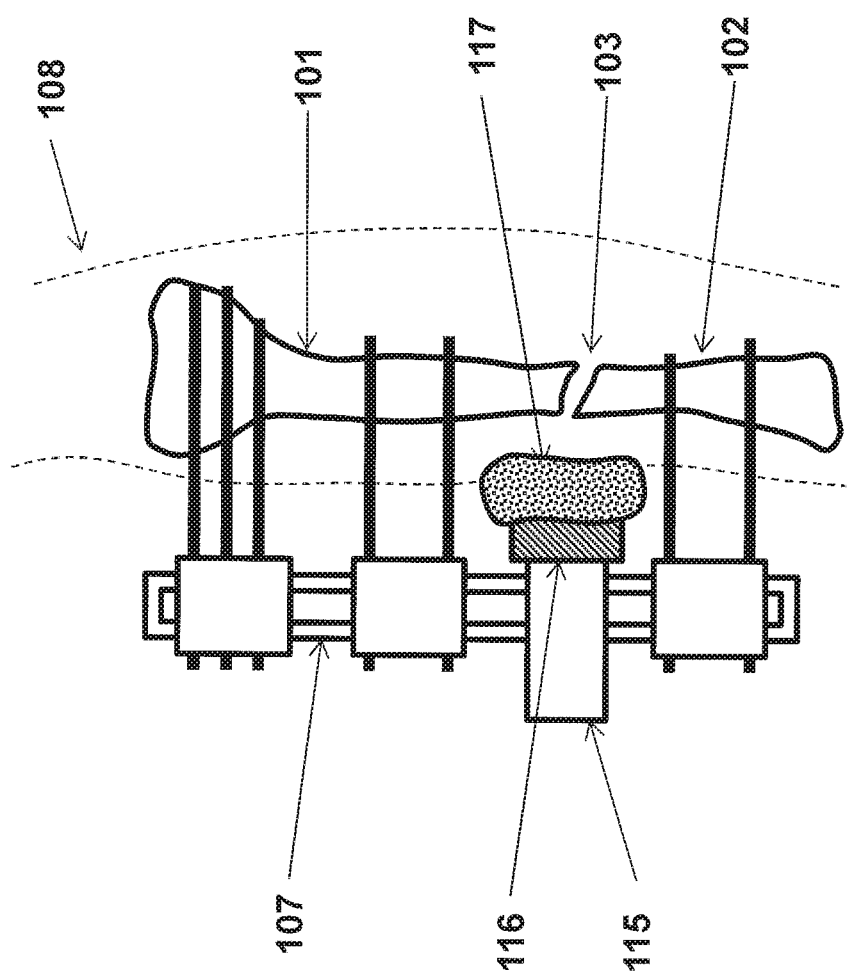

For example, consider the rail fixator shown in the schematic of FIG. 21 and redrawn in FIG. 23. To provide the means of adjustably applying pressure to the soft tissue adjacent to the indicated fracture or subperiosteal osteotomy 103, a block 115 is clamped to the rail 107 close to the location of the fracture or subperiosteal osteotomy 103. The block 115 is adjustable along the length of the rail 107. An elastic member 116, preferably consisting of at least one helical spring member, is attached to the block 115 on its limb 108 side as shown in FIG. 23, and is used to apply pressure to the soft tissue adjacent to the bone fracture or subperiosteal osteotomy 103 via the pressure distributing intermediary contact material 117. The pressure applied to the soft tissue can be adjusted by clamping the block 115 closer or further from the limb 108.

Figure 24:
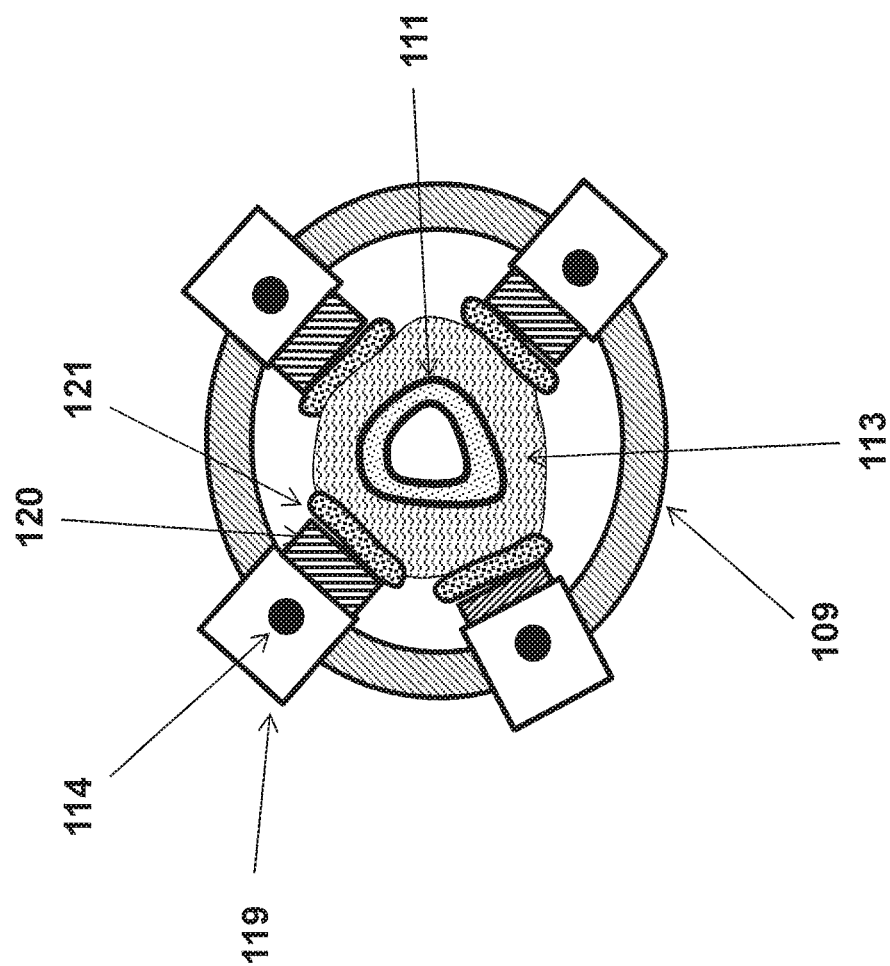

The method of adjustably applying pressure to the soft tissues adjacent to the indicated fracture or subperiosteal osteotomy site is shown using the cross-sectional view "B-B" of FIG. 22 shown in FIG. 24. In a manner similar to that described for the rail fixator of FIG. 23, blocks 119 are attached to at least one and preferably more than one of the threaded rods 114 at the level of the indicated fracture or subperiosteal osteotomy 118, FIG. 22, as shown in FIG. 24. In FIG. 24, blocks 119 are seen to be attached to all four connecting threaded rods 114. The blocks 119 are adjustable along the length of the threaded rods 114 and can be readily positioned facing the site of the fracture or subperiosteal osteotomy 118. An elastic member 120, preferably consisting of at least one helical spring member, is attached to the block 119 on its limb 113 side as shown in FIG. 24, and is used to apply pressure to the soft tissue adjacent to the bone fracture or subperiosteal osteotomy 118 via the pressure distributing intermediary contact material 121. The pressure applied to the soft tissue can be adjusted by clamping the block 119 closer. or further from the limb 113.

It is appreciated by those skilled in the art that any of the methods described in the embodiments of FIGS. 1-3, 5-6, 7A and 7B and 13-20 may also be used for adjusting the pressure applied to the soft tissue by the pressure distributing intermediary contact material 117 and 121, shown respectively in FIGS. 23 and 24.

Tenth Embodiment

In the above described embodiments, different methods, devices and configurations are disclosed for the application of the desired level of pressure to soft tissues over the bone fracture site in the absence or presence of internal or external fixation devices.

In this embodiment, new methods and related apparatuses for applying the desired level of pressure to soft tissues over bone fracture site in the absence or presence of internal or external fixation devices is disclosed. In the disclosed methods and related apparatus embodiments, the application of the desired level of pressure to the intended area of soft tissue is achieved by applying a certain level of vacuum to an enclosed volume.

The application of reduced pressure to a wound can provide such benefits as faster healing, increased formation of granulation tissue, closure of chronic open wounds, reduction of bacterial density within wounds, inhibition of burn penetration, and enhancement of flap and graft attachment.

The present embodiment is directed to an apparatus that includes a gas and/or fluid substantially impermeable and flexible cover, such as one made of medical grade sheet of polymer material, such as, for example, polyethylene, which can be sealed over a wound and/or fracture site. A porous open-cell foam or a relatively rigid porous screen can be placed over the wound and/or fracture and underneath the cover. A vacuum pump is then used to apply a negative pressure relative to the outside atmospheric pressure (suction) to the enclosed volume. A more detailed discussion and illustration of the disclosed apparatus is provided below.

The wound cover of the reduced pressure application appliance is substantially sealed to the surface of the tissue surrounding the wound and/or area of fracture, thereby enclosing the wound and/or fracture within a sealed volume. To aid in substantially sealing the wound cover to the tissue surrounding the wound and/or area of fracture, an adhesive, or other suitable material that is capable of maintaining the wound cover in contact with a person's skin, can be applied to the underside of the wound cover around its periphery. The generally flexible wound cover allows the wound cover o conform to the surface of the region of the body to be covered.

Other seals may be a separate sealing member, such as an adhesive strip, for positioning and substantially sealing the wound cover around the periphery of the wound and/or fracture.

A port can be provided in the wound cover for connection to a vacuum source.

The disclosed apparatus can use a porous wound screen for placement in the wound or in position overlying the wound and/or fracture to prevent overgrowth of tissue during treatment. The screen is sufficiently porous to permit gas and/or fluid to flow therethrough. The screen may be in the form of a sponge or open-cell foam material, or a rigid or semi-rigid screen.

In operation, a method of treating damage is provided which comprises applying a negative or reduced pressure to a wound and/or fracture over an area sufficient to promote the migration of epithelial and subcutaneous tissue toward the wound and/or fracture and for a length of time that is sufficient to facilitate closure of the wound and/or healing of the fracture. In burn wound treatment, the applied negative pressure assists in increasing blood flow to the region and extracting edema to facilitate healing and inhibiting the progression in the depth of the burn.

The methods and apparatus of the present disclosure are directed to the formation of an enclosed volume over a region of a patient's skin (soft tissues), possibly over a fractured bone, to apply a prescribed positive pressure to the region of skin, without causing suction over other regions of the skin which would otherwise enhance blood flow, to reduce flood flow over the region and thereby enhance healing and healing of the bone fracture.

The present disclosure is directed to at least the following advantages: (a) the applied pressure over the intended surface can be made to become relatively uniform or have a prescribed distribution profile; (b) the apparatus can substantially keep the applied pressure level after vacuum application has ceased for at least a certain length of time, thereby eliminating or reducing the number of vacuum applications; (c) in an embodiment discussed below a vacuum generating machine is not needed and the required vacuum is generated by the application of pressure by hand on the surface of the applied cover; and (d) pressure can be applied to the intended region without substantially exerting a "shearing" pull on the skin and soft tissues.

Typical apparatus for applying negative pressure to wounds are designed to increase blood flow to that region of the body, which is substantially opposite of what is disclosed below by the disclosed apparatus.

Figure 25:
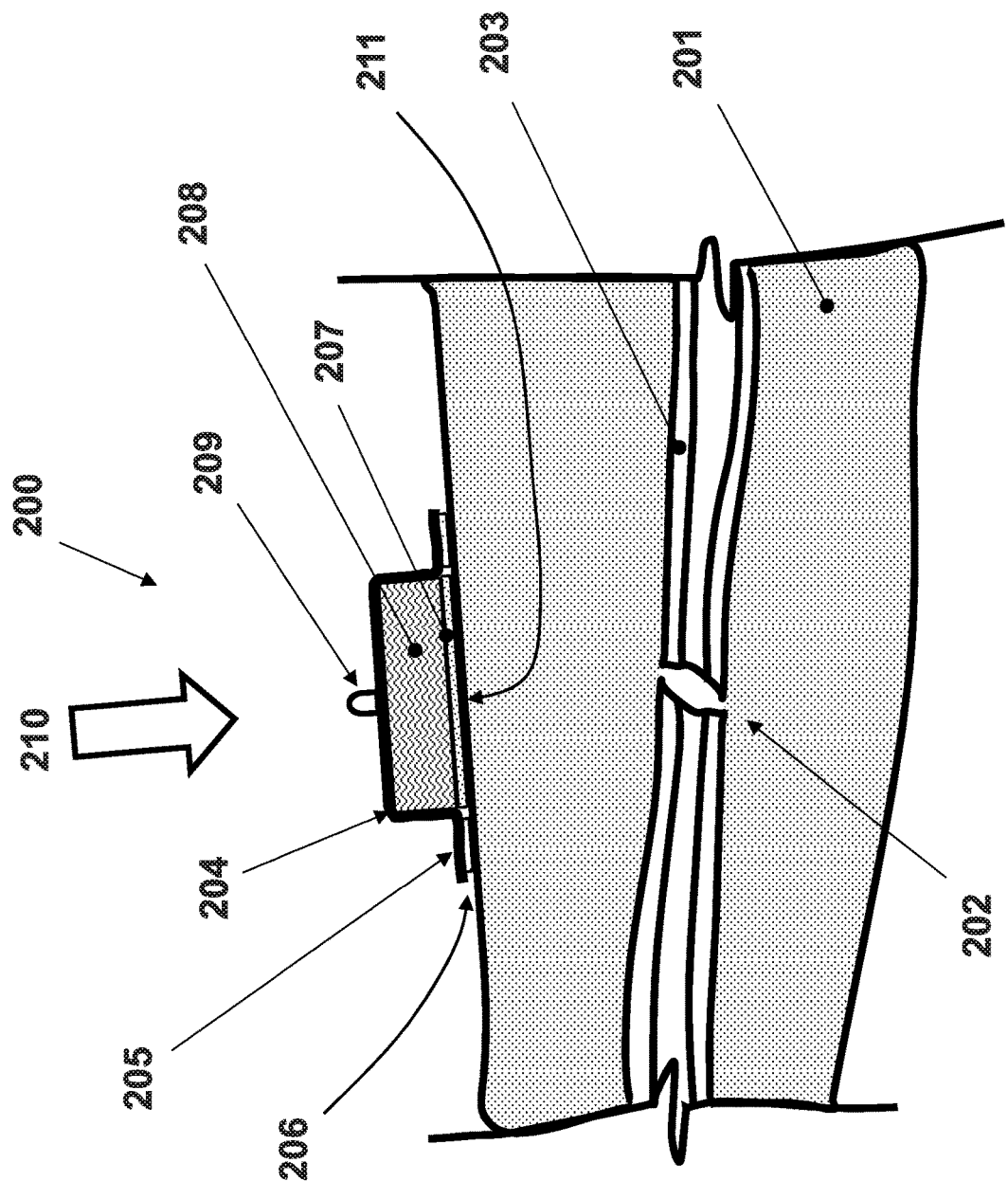
FIG. 25 illustrates a side view of an embodiment of a pressure applicator.

Referring to FIG. 25, the pressure applicator embodiment 200 of the present disclosure is shown. The pressure applicator 200 is shown attached to a skin surface of a patient limb 201 in a region over the fracture 202 of the bone 203. Although pressure applicator 200 is shown on a limb 201 in FIG. 25, in other embodiments pressure applicator 200 can be placed over a fracture at any location of a patient's body.

Figure 26:
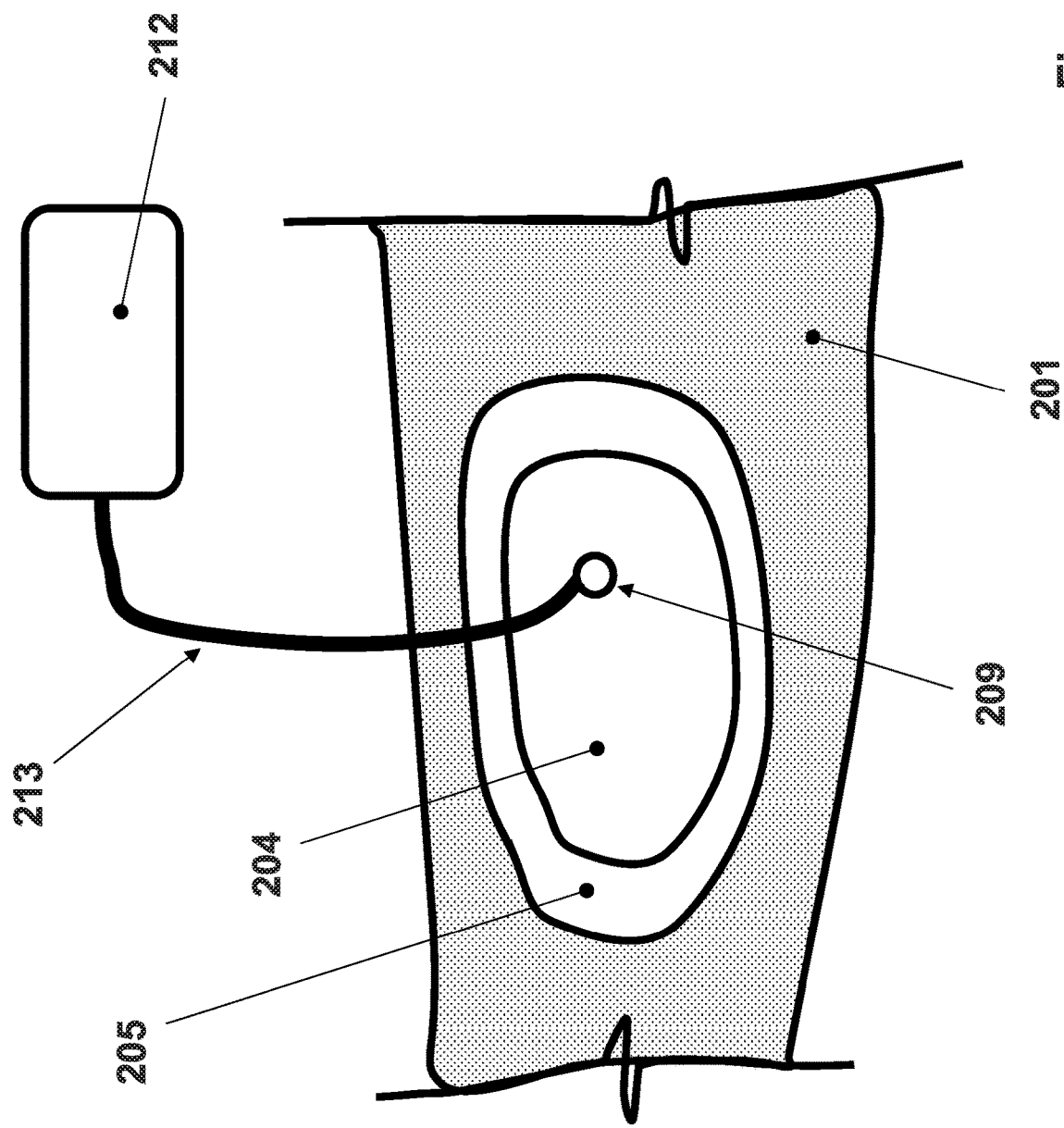
FIG. 26 illustrates a top view of an embodiment of the pressure applicator.

A top view of the pressure applicator 200 (as seen in the direction of the arrow 210 of FIG. 25) is shown in FIG. 26. The pressure applicator 200 consists of a fluid and gas substantially impermeable, flexible sheet cover 204, such as one made of medical grade sheet of polymer material, such as, for example, polyethylene film, which is substantially sealed on its periphery 205 by a separate sealing member, such as an adhesive strip 206, or in other embodiments an applied sealing adhesive to a surface of the sheet cover 204 contacting the skin region 211.

A fluid and gas substantially impermeable sheet 207, such as an elastomeric material like a rubber or other suitably flexible material, is provided over the region of the limb 201 to which the pressure is to be applied. Optionally, the surface of the sheet 207 in contact with the patient skin may be covered with a thin layer of moisture absorbing fabric or the like such a layer of cotton fabric (not shown) to minimize skin sensitivity and perspiration.

Attached to the sheet 207 is a relatively thick member 208, which can be relatively flexible axially (in the direction of the arrow 210 as seen in FIG. 25), and relatively less flexible in the lateral direction. The member 208 is not fully solid and is provided with an internal structure (as provided below), which allows the member 208 to deform elastically when subjected to an external force in the direction of the arrow 210. The member 208 is also flexible in bending so that it can be bent to conform to the surface area of the limb 201 over which it is to be positioned. The member 208 may also be a composite structure, so that it includes more flexibility in the axial direction as compared to the lateral direction, as further described below. The sheet 207 can be an integral part of the member 208 or the sheet 207 can be securely attached to the surface of the member 208.

The pressure applicator 200 is applied to the desired site and assembled such that sheet cover 204 is in close contact with the sheet 207 and member 208. The sheet cover 204 is also provided with a port 209, which is optionally connected by a hose 213 to a vacuum pump system as shown in FIG. 26, or the like through which a means of reducing pressure inside the sealed volume between the sheet cover 204 and the covered skin region 211 of the patient's limb 201. The vacuum pump system 212 may be of electrically or manually operated type and can apply a desired level of vacuum pressure.

The pressure inside the enclosed volume (between the sheet cover 204 and the covered skin region 211 of the patient limb 201) becomes lower than the atmospheric pressure and since sheet cover 204 is deformable, much of or nearly all the difference between the atmospheric pressure and the reduced pressure within the enclosed volume is applied to the outer surface of the member 208 by the contacting surface of the sheet cover 204.

As the reduced pressure is applied to the enclosed volume, parts of the sheet cover 204 around the sides of the member 208 becomes loose. Member 208 can include a number of sheets forming member 208 to aid in a greater lateral stiffness compared to the axial stiffness. Examples of these sheets that can compose member 208 are shown in FIGS. 27 and 28. Also, the sides of the member. 208 can be provided with openings between the laterally relatively stiff sheets (between the sheets 216 in FIG. 28 and between the sheets 223 FIG. 29) or between the relatively soft and deformable material (material 215 between the thin films 214 in FIG. 27), to account for the loose side areas of member 208.

Thus, sheet cover 204, around the sides of the member 208, can apply a force downward to the sides of the member 208, while the vacuum pressure is applied, while being drawn closer in the perpendicular direction of member 208. The resulting pressure applied to the top surface of the member 208 would cause it to axially deform a certain amount while transmitting the pressure to the surface of the skin 211, of the patient limb 201, over the bone fracture 202 via the sheet 207, as seen in FIG. 25.

The member 208 is configured to not deform in the lateral direction to a substantial. degree (direction substantially perpendicular to the direction of the arrow 210 and substantial parallel to the skin surface 211 in FIG. 25) because such lateral contraction of the member 208 can cause the application of a shearing force to the skin 211 when the sheet cover 204 is being subject to a reduction in atmospheric pressure.

Figure 29:
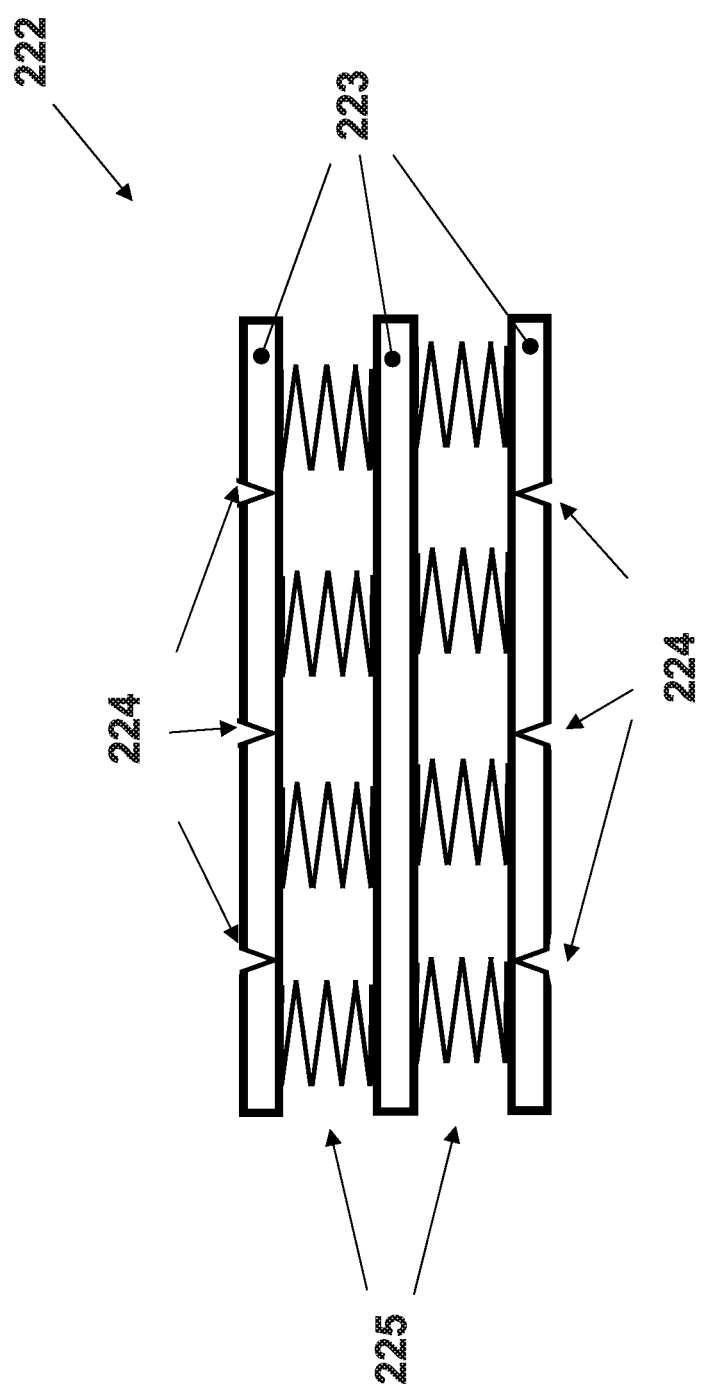
FIG. 29 is a cross-sectional view of a member of the pressure applicator.

As discussed above, member 208 can be an embodiment as shown in FIG. 25, and can also be an embodiment selected from the non-limiting examples shown in FIGS. 27, 28 and 29.

Another embodiment of member 208, is shown in the cross-sectional view of FIG. 27 and identified by the numerical identifier 220. In this embodiment, the member 220 is constructed with at least two thin films 214, which are relatively flexible in bending but relatively rigid laterally. The thin films 214 are separated by layers of sponge-like porous elastic foam 215 or the like, with high interconnected relative void volume. To assist bending of the thin films 214 over curved surfaces, they are provided with longitudinal and transverse v-shaped (or functionally similarly shaped) grooves 217. In this embodiment, the thin films 214 provide lateral rigidity of the member 220 while allowing it to be relatively flexible in bending to conform to various curved surfaces of a patient's body. The layers of foam 215 provided the indicated axial elasticity (in the direction of the arrow 210 in FIG. 25, i.e., in the direction of being deformed to bring the thin films 214 closer. together). The interconnected voids inside the foam 215 allows the vacuum pump 212 to suction air out of the sealed volume between the sheet cover 204 and the covered skin region 211.

A third embodiment of member 208, is shown in the cross-sectional view of FIG. 28 and identified by the numerical identifier 221. In this embodiment, the member 221 is constructed with at least two sheets 216, which are similar to the thin films 214 of the embodiment of FIG. 27, i.e., are relatively flexible in bending but relatively rigid laterally. The sheets 216 are held apart as shown in FIG. 28 by elastic elements, such as curved (or another suitable shape) forms 218 that run along the length of the member 221. The forms 218 function in a similar way to foam 215 of FIG. 27, to provide axial elasticity while providing minimal resistance to bending of the member 221. To assist bending of the sheets 216 over curved surfaces, the sheets 216 can be provided with longitudinal and transverse v-shaped (or another suitably shaped) grooves 219. In this embodiment, the sheets 216 add to lateral rigidity of the member 221 while allowing it to be relatively flexible in bending to conform to various curved surfaces of the patient body. The curved members 218 can be made of the same material as the sheets 216, and are designed to provide the desired level of axial stiffness between the sheets 216. In another embodiment, the members 218 may be integral to the sheets 216.

The interconnected voids between the forms 218 allow the vacuum. pump 212 to suction air out of the sealed volume between the sheet cover 204 and the covered skin region 211. To assist this pressure reduction process, spaced holes 230 can be also provided in the curved members 218 for free flow of air between the sheets 216.

A fourth embodiment of member 208, is shown in FIG. 29 and identified by the numerical identifier 222. In this embodiment, the member 222 is constructed with at least two sheets 223, which are similar to the thin films 214 of the embodiment of FIG. 27, i.e., are relatively flexible in bending but relatively rigid laterally. The sheets 223 are supported at a distance between themselves as shown in FIG. 29 by elastic elements such as springs 225 which are spaced between the sheets 223. The springs 225 function in a similar way to the sponge-like porous elastic foam 215 to provide axial elasticity while providing minimal resistance to bending of the member 222. To assist bending of the sheets 223 over curved surfaces, they can include longitudinal and transverse v-shaped (or another suitable shape) grooves 224. In this embodiment, the sheets 223 add to lateral rigidity of the member 222 while allowing it to be relatively flexible in bending to conform to various curved surfaces of a patient's body. The springs 225 can be configured to provide the desired level of axial stiffness between the sheets 223. The space provided between the sheets 223 allows the vacuum pump 212 to suction air out of the sealed volume between the sheet cover 204 and the covered skin region 211.

The embodiments of the member 208 of FIGS. 27, 28 and 29 are designed to provide a relatively uniform pressure over the surface 211 of the limb 201 (as seen in FIG. 25). The embodiment 222 in FIG. 29 can be configured to provide a non-uniform pressure distribution over the surface 211 of the limb 201 by using springs of varying stiffness over the area of the member 208. For example, by providing stiffer middle springs as seen in the cross-sectional view of FIG. 29, the pressure over the middle region of the surface 211 of the limb 201 would be higher than those of the outer regions upon a reduction in pressure.

Nonuniform pressure application over the surface 211 of the skin and thereby underlying soft tissue at the bone fracture site 202 can be advantageous when dealing with bones such as the clavicle. For bones such as the clavicle, where application of a more uniform pressure along the length of the bone over the fracture site 202 (as shown in the longitudinal cross-sectional view of FIG. 31A), with the pressure decreasing from its mid-point high in both lateral directions (as shown in the transverse cross-sectional view of FIG. 31B) can be advantageous. In the longitudinal cross-sectional view of FIG. 31A, a section of the clavicle bone 231 with its fracture 232 is shown together with a section of soft tissues 233 around it to which a uniform pressure in the longitudinal direction (as shown by the arrows 234) are to be applied by the pressure applicator 200 of the present disclosure.

Figure 31B:
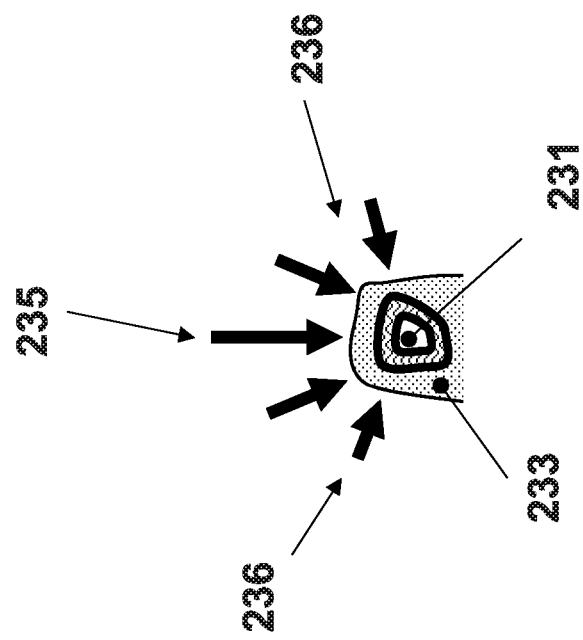
FIG. 31B is a transverse cross-sectional view of a bone receiving pressure.
Figure 31A:
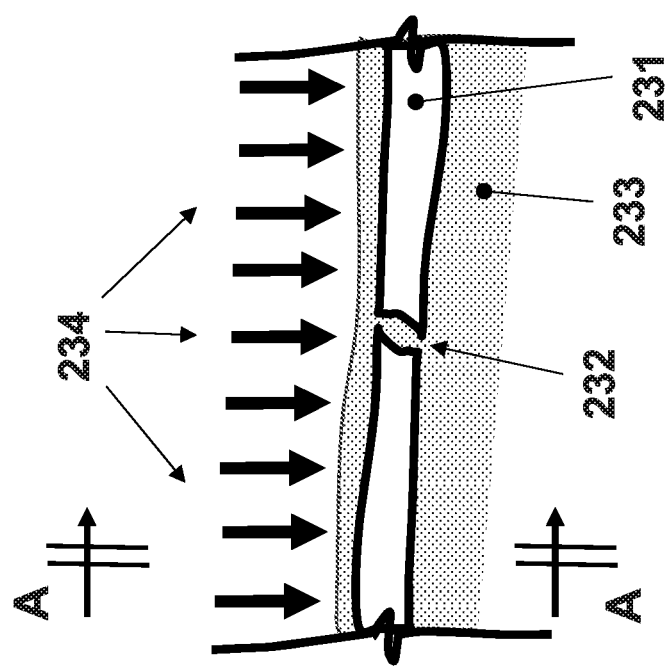
FIG. 31A is a longitudinal cross-sectional view of a bone receiving pressure.

In the example of the clavicle bone 231 or the like, the applied pressure 234 can have a distribution like that shown in the cross-sectional view A-A in FIG. 31B, i.e., higher pressures 235 in the middle with lower pressures 236 on the sides. Such a force distribution can be achieved by the member 208, when constructed as the member 222 of FIG. 29 configured to include stiffer springs where higher pressure levels are desired to be applied to the soft tissues.

The desired pressure distribution can also be obtained using member 221 of FIG. 28, since the member 221 can be constructed to be stiffer in the direction perpendicular to the plane of FIG. 28, and by aligning the member 221 along the length of the clavicle bone 231. The lower side pressures 236 can also be achieved by cutting portions of the side members 218.

Figure 30:
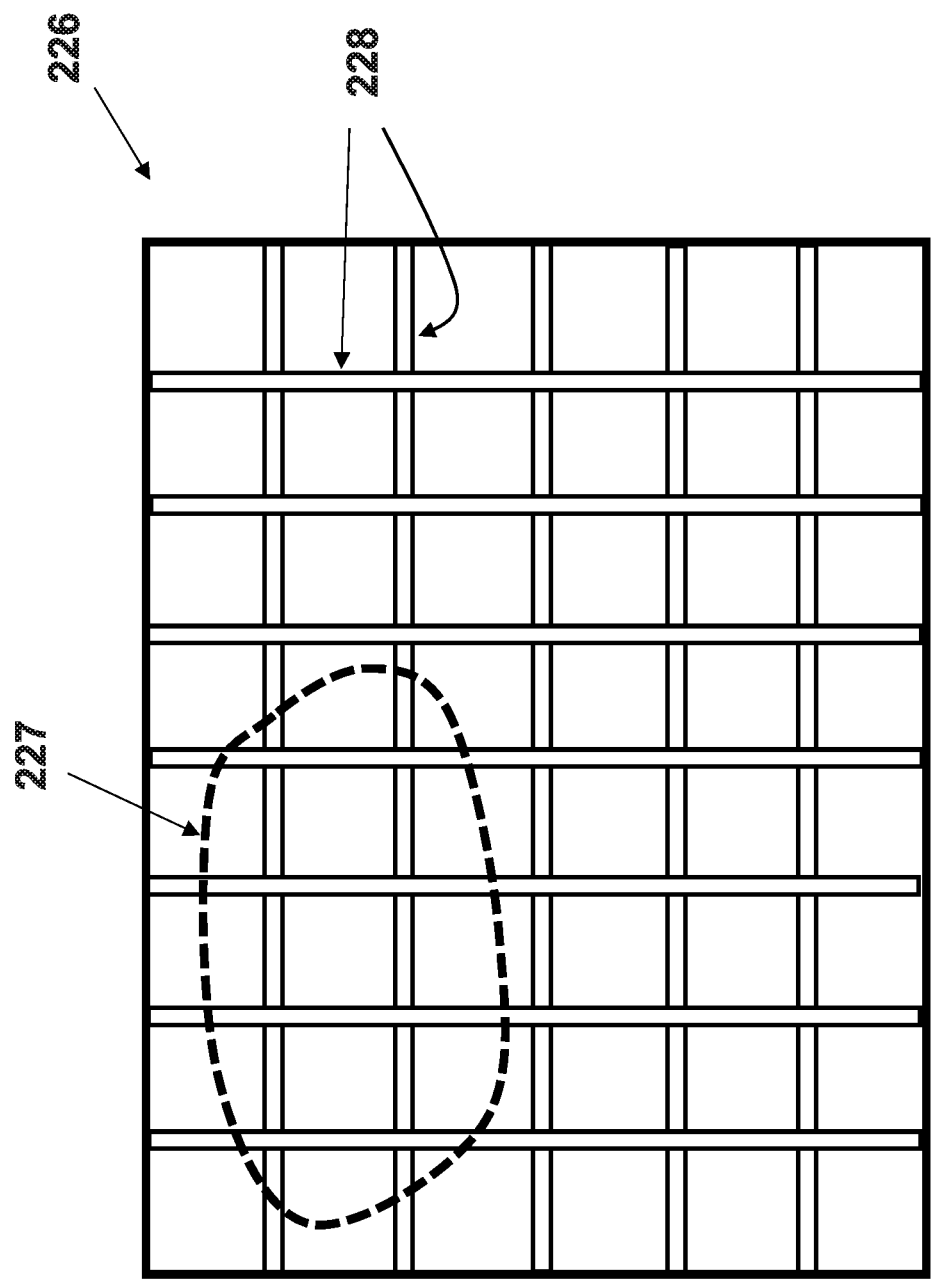
FIG. 30 is a top view of another embodiment of a member of the pressure applicator.

In other embodiments, the member 208 of FIGS. 27, 28 and 29 can be fabricated as relatively large blocks such as the block 226 shown in the top view of FIG. 30. A user could then cut the desired shape, for example the one shown by the dashed line 227. In FIG. 30 the longitudinal and transverse v-shaped grooves (217, 219 and 224 in FIGS. 27, 28 and 29, respectively) are shown and indicated by numeral 228.

In another pressure applicator embodiment of the present disclosure, the embodiment 200 of FIG. 25 can be modified to enable a user not to include the vacuum pump system 212 shown in FIG. 26 and instead manually operate an applicator to achieve the desired level of soft tissue pressure over the surface 211 of the limb 201. The modification can include the replacement of the port 209 with a one-way valve that is directed for exhausting air from the sealed volume between sheet cover 204 and the covered skin region 211 of the patient limb 201.

After the modified pressure applicator is applied over the bone fracture 202 (as shown in FIG. 25), a physician or the patient themselves can generate the desired level of soft tissue pressure by applying pressure to the top surface of the local pressure applicator to exhaust the desired amount of air trapped inside the sealed volume. In addition, if the soft tissue pressure drops below the desired level, the user can similarly bring the pressure up to the prescribed level. In addition, the said one-way valve can be adjustable so that it can open to relieve the applied soft tissue pressure.

The pressure applicators of the present disclosure may be applied partially or completely around a limb, and in the presence or absence any external fixations such as those shown in FIGS. 23 and 24. In addition, when applied to a limb in the presence of external fixation pins, the present embodiments can reduce pulling of the skin surrounding the pins.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. A pressure application device comprising:
    a sheet cover configured to extend over a portion of a patient's skin corresponding to a bone fracture under the skin, the sheet cover configured to form an enclosed volume between the portion of the patient's skin and the sheet cover, wherein the sheet cover comprises a vacuum port, the vacuum port configured to apply a vacuum to withdraw a gaseous volume from the enclosed volume;
    a member, the member configured to be in the enclosed volume, the member configured to deform elastically, in response to the vacuum, in at least a direction towards the skin and apply a force to the fracture; and
    a sheet, the sheet configured to extend over the portion of the patient's skin, a first surface of the sheet in contact with the patient's skin, an entire second surface of the sheet in contact with the member, the first surface of the sheet opposite to the second surface of the sheet, and wherein a first surface of the member is in contact with the sheet cover, a second surface of the member is in contact with a sheet.

2. The pressure application device of claim 1, wherein the member deforms more in a first direction than a second direction.

3. The pressure application device of claim 2, wherein the first direction is an axial direction and the second direction is a lateral direction.

4. The pressure application device of claim 1, further comprising a vacuum system configured to operably connect to the port and withdraw at least a portion of the gaseous volume from within the enclosed volume.

5. The pressure application device of claim 1, wherein the sheet cover is operably connected to a portion of a person's skin with an adhesive material around a periphery of the sheet cover.

6. A method of applying a pressure application device to a portion of a patient's skin, the method comprising
    positioning a member and a sheet on the portion of the patient's skin corresponding to a bone fracture under the skin, a first surface of the sheet in contact with the patient's skin, an entire second surface of the sheet in contact with the member, the first surface of the sheet opposite to the second surface of the sheet;
    applying a sheet cover to the portion of the patient's skin by adhering a periphery of the sheet cover to the portion of the patient's skin over the member to create a sealed, enclosed volume between the portion of the patient's skin and the sheet cover, wherein a first surface of the member is in contact with the sheet cover, a second surface of the member is in contact with a sheet; and
    applying a vacuum to the enclosed volume, such that the sheet cover applies a force to the member and the sheet, wherein the member is configured to deform elastically in at least a direction towards the skin, and wherein the member applies a force to the fracture.

7. The pressure application method of claim 6, wherein the member deforms more in a first direction than a second direction.

8. The pressure application method of claim 7, wherein the first direction is an axial direction and the second direction is a lateral direction.

9. The pressure application method of claim 6, wherein a longitudinal axis of the member is applied on the patient's skin along a length of the fractured bone.

10. A method of applying a pressure application device to a portion of a patient's skin, the method comprising:
    applying the pressure application device to the portion of the patient's skin, the pressure application device comprising:

a sheet cover configured to extend over a portion of a patient's skin corresponding to a bone fracture under the skin, the sheet cover configured to form an enclosed volume between the portion of the patient's skin and the sheet cover, wherein the sheet cover comprises a vacuum port, the vacuum port configured to apply a vacuum to withdraw a gaseous volume from the enclosed volume;

a member, the member configured to be in the enclosed volume, the member configured to deform elastically, in response to the vacuum, in at least a direction towards the skin and apply a force to the fracture; and a sheet, the sheet configured to extend over the portion of the patient's skin, a first surface of the sheet in contact with the patient's skin, an entire second surface of the sheet in contact with the member, the first surface of the sheet opposite to the second surface of the sheet, and wherein a first surface of the member is in contact with the sheet cover, a second surface of the member is in contact with a sheet; and removing at least a portion of the gaseous volume from the enclosed volume through the port.

11. The method of claim 10, wherein the sheet cover is operably connected to a portion of a person's skin with an adhesive material around a periphery of the sheet cover.

\* \* \* \* \*